US009897530B2

(12) United States Patent
Durack et al.

(10) Patent No.: US 9,897,530 B2
(45) Date of Patent: Feb. 20, 2018

(54) COMPENSATION OF MOTION-RELATED ERROR IN A STREAM OF MOVING MICRO-ENTITIES

(75) Inventors: Gary Durack, Urbana, IL (US); Stephen D. Fleischer, Honolulu, HI (US); Jeremy Hatcher, Urbana, IL (US); David Roberts, Evans, GA (US); Michael Zordan, Champaign, IL (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 149 days.

(21) Appl. No.: 14/240,830

(22) PCT Filed: Aug. 24, 2012

(86) PCT No.: PCT/US2012/052204
§ 371 (c)(1),
(2), (4) Date: Feb. 25, 2014

(87) PCT Pub. No.: WO2013/028948
PCT Pub. Date: Feb. 28, 2013

(65) Prior Publication Data
US 2014/0212917 A1  Jul. 31, 2014

Related U.S. Application Data

(60) Provisional application No. 61/527,340, filed on Aug. 25, 2011.

(51) Int. Cl.
*G01N 15/14* (2006.01)
*G01N 15/10* (2006.01)

(52) U.S. Cl.
CPC ..... *G01N 15/1404* (2013.01); *G01N 15/1427* (2013.01); *G01N 15/1429* (2013.01);
(Continued)

(58) Field of Classification Search
CPC ................ G01N 33/48; G01N 15/1404
See application file for complete search history.

(56) References Cited

U.S. PATENT DOCUMENTS 4,184,766 A  1/1980 Hogg
4,318,483 A  3/1982 Lombardo et al.
(Continued)

FOREIGN PATENT DOCUMENTS

EP       0 412 431 A2    2/1991
WO    WO 99/44037 A1    9/1999
(Continued)

OTHER PUBLICATIONS

Patent Application No. 201280003477.4, Chinese Patent Office, Office Action, dated Mar. 2, 2015.
(Continued)

*Primary Examiner* — David Porta
*Assistant Examiner* — Hugh H Maupin
(74) *Attorney, Agent, or Firm* — Ice Miller LLP

(57) ABSTRACT

Apparatus and methods for detecting, characterizing, and compensating motion-related error of moving micro-entities are described. Motion-related error may occur in streams of moving micro-entities, and may represent a deviation in and expected arrival time or an uncertainty in position of a micro-entity within the stream. Motion-related error of micro-entities is observed in a flow cytometer, e.g., as pulse jitter, and is found to have a functional dependence on a parameter of the system. The pulse jitter can be compensated, according to one embodiment, by adjusting data acquisition observation windows. For the flow cytometer, a reduction of pulse jitter can improve measurement accuracy, resolution of doublets, system throughput, and enable an increase in an interrogation region for probing the micro-entities.

12 Claims, 11 Drawing Sheets

(52) U.S. Cl.
CPC . *G01N 15/1459* (2013.01); *G01N 2015/1006* (2013.01); *G01N 2015/1075* (2013.01); *G01N 2015/149* (2013.01); *G01N 2015/1415* (2013.01); *G01N 2015/1438* (2013.01); *G01N 2015/1477* (2013.01)

(56) References Cited

U.S. PATENT DOCUMENTS

| | | | |
|---|---|---|---|
| 4,325,483 | A | 4/1982 | Lombardo et al. |
| 4,863,264 | A | 9/1989 | Miyake et al. |
| 5,150,313 | A | 9/1992 | Van Den Engh et al. |
| 5,548,395 | A | 8/1996 | Kosaka |
| 6,079,836 | A | 6/2000 | Burr et al. |
| 6,248,590 | B1 * | 6/2001 | Malachowski ............... 436/63 |
| 6,589,792 | B1 * | 7/2003 | Malachowski .... G01N 15/1404 209/127.4 |
| 6,608,680 | B2 | 8/2003 | Basiji et al. |
| 7,274,316 | B2 | 9/2007 | Moore |
| 7,653,509 | B2 * | 1/2010 | Bagwell .................... 702/181 |
| 2005/0112541 | A1 | 5/2005 | Durack et al. |
| 2006/0263829 | A1 | 11/2006 | Evans et al. |
| 2008/0087068 | A1 | 4/2008 | Roth |
| 2009/0071225 | A1 | 3/2009 | Schilffarth |
| 2010/0172898 | A1 | 7/2010 | Doyle et al. |
| 2010/0297759 | A1 * | 11/2010 | Kanda ........................ 435/374 |
| 2010/0328662 | A1 | 12/2010 | Vacca et al. |
| 2014/0220621 | A1 | 8/2014 | Durack et al. |

FOREIGN PATENT DOCUMENTS

| | | |
|---|---|---|
| WO | WO 2011/112697 A1 | 9/2011 |
| WO | WO 2013/028947 A1 | 2/2013 |
| WO | WO 2013/028948 A1 | 2/2013 |

OTHER PUBLICATIONS

Patent Application No. 201280003477.4, Chinese Patent Office, Translation of Office Action, dated Mar. 2, 2015.
[No Author Listed], Synergy Operator's Guide. iCyt Mission Technology. Oct. 2011. 217 pages.
International Search Report and Written Opinion dated Nov. 6, 2012 in connection with International Application No. PCT/US2012/052204.
International Search Report and Written Opinion dated Nov. 16, 2012 in connection with International Application No. PCT/US2012/052202.
Extended European Search Report dated Feb. 5, 2015 in connection with European Application No. 12826157.5.
Extended European Search Report dated Feb. 5, 2015 in connection with European Application No. 12826436.3.

* cited by examiner

COMPENSATION OF MOTION-RELATED ERROR IN A STREAM OF MOVING MICRO-ENTITIES

CROSS REFERENCE TO RELATED APPLICATIONS

This application claims priority under 35 U.S.C. 119(e) to U.S. provisional application No. 61/527,340 titled, "System and Method for Correction of Pulse Jitter in Flow Cytometers" and filed on Aug. 25, 2011, which is incorporated by reference in its entirety.

FIELD

Methods and apparatus described relate to compensating motion-related error in a stream of moving micro-entities. Evaluation and compensation of higher-order motion characteristics can improve measurements of and/or operations on moving micro-entities. Areas of applications include flow cytometry, microfluidics, and nanofabrication.

BACKGROUND

The areas of analysis, development, and fabrication of micro-entities have become widespread in various technologies in recent years. Micro-entities, as used herein, may include cells, microorganisms, micro- or nano-particles, droplets, molecules, proteins, peptides, calibration particles, and microfabricated structures such as microelectromechanical (MEM) structures, microelectronic chips, and microsensors. A micro-entity may include any entity (manmade or naturally occurring) that has a maximum dimension less than about 1 millimeter (mm). In some research, medical, or fabrication applications, micro-entities may be moved in a stream in large numbers. The stream may be part of a system that controls the movement and the metering of micro-entities into the stream. One example application is the characterization and sorting of cells in a flow cytometer. Another example may be movement, observation, and sorting of micro-entities in microfluidic channels.

In some applications, it may be desirable to know the locations precisely of a selected micro-entity within the moving stream at one or more selected times, or in other embodiments, to know the times precisely when a selected micro-entity will arrive at one or more locations. For example and referring to FIG. 1, a micro-entity 125 may move in a stream 120 of micro-entities. A stream 120 of micro-entities may comprise a fluid stream (e.g., a gas, liquid, or particulate stream) or flow path capable of conveying the micro-entities. The micro-entities may be in suspension in the stream. In some cases, a stream 120 of micro-entities may comprise a dense collection of the micro-entities that moves in a stream-like manner. A stream 120 of micro-entities may be conveyed by any combination of mechanical, electrical, and magnetic means.

A micro-entity 125 may be detected at a first location $P_1$ at a first time $t_1$, and it may be desirable to know at what time $t_2$ the micro-entity 125 will arrive at a pre-selected second location $P_2$ or a plurality of other locations along the stream. Conversely, the micro-entity 125 may be detected at the first location $P_1$ at a first time $t_1$, and it may be desirable to know at what location $P_3$, or locations, the micro-entity 125 will be after a pre-selected elapsed time $t_3$, or times. In the former case, predicting the arrival time $t_2$ can be useful in determining when a measurement or an operation (e.g., a sorting operation, an imaging operation, a charging operation, a transforming operation, an illumination of the entity, a signal detection etc.) may be performed on the micro-entity at the second location $P_2$. In the latter case, predicting the location $P_3$ of the micro-entity 125 may be useful for precisely tracking the movement and/or evolution of the entity in the stream, e.g., acquiring and overlaying multiple images of the micro-entity as it moves along the stream.

One method for predicting the arrival time $t_2$ or location $P_3$ of a micro-entity in a moving stream is to calculate an expected value of $t_2$ or $P_3$ based upon an average stream velocity $v_{avg}$. The average stream velocity may be measured or determined in any suitable way. If $v_{avg}$ is found or known, then either $t_2$ or $P_3$ may be determined through the relation $d=v_{avg} \times t$, where d is the distance traveled by the micro-entity 125 in an elapsed time t. An alternative method for predicting an arrival time $t_2$ at a predetermined location $P_2$ is to add an average transit time or delay time $\Delta t_{avg}$ to the value of $t_1$ after observing the entity at $P_1$. The time $\Delta t_{avg}$ may be measured or determined in any suitable way. In some cases, these methods of predicting arrival times or locations of moving micro-entities may be sufficient.

Flow cytometers are examples of systems which utilize streams to transport micro-entities for purposes of characterizing and sorting the micro-entities, such as biological cells. Flow cytometers are used widely for rapidly analyzing heterogeneous cell suspensions to identify constituent subpopulations. Examples of the many applications where flow cytometry cell sorting is finding use include isolation of rare populations of immune system cells for AIDS research, isolation of genetically atypical cells for cancer research, isolation of specific chromosomes for genetic studies, and isolation of various species of microorganisms for environmental studies. For example, fluorescently labeled monoclonal antibodies are often used as "markers" to identify immune cells such as T lymphocytes and B lymphocytes, clinical laboratories use this technology to count the number of "CD4 positive" T lymphocytes in HIV infected patients, and they also use this technology to identify cells associated with a variety of leukemia and lymphoma cancers.

Recently, two areas of interest are moving cell sorting towards clinical, patient-care applications, rather than strictly research applications. First is the move away from chemical pharmaceutical development to the development of biopharmaceuticals. For example, many new cancer therapies utilize biological material. These include a class of antibody-based cancer therapeutics. Cell sorters can play an important role in the identification, development, purification and, ultimately, production of these products.

Related to this is a move toward the use of cell replacement therapy for patient care. Much of the current interest in stem cells revolves around a new area of medicine often referred to as regenerative therapy or regenerative medicine. These therapies may often require that relatively rare cells be isolated from patient tissue. For example, adult stem cells may be isolated from bone marrow and ultimately used as part of a re-infusion back into the patient from whom they were removed. Flow cytometry and cell sorting are important tissue processing tools that may enable delivery of such therapies.

SUMMARY

Apparatus and methods for compensating motion-related error of micro-entities moving in a stream are described. Motion-related error of moving micro-entities may include any type and form of error that contributes to a deviation from an expected arrival time or expected location of a micro-entity at a second location or second time given the detection of the same micro-entity at a first location or first time. Motion-related errors of moving micro-entities may comprise real physical movement and/or apparent movement of the micro-entities. It will be appreciated that motion-related errors can pertain to multiple arrival times and locations at various points along a stream. The expected arrival time(s) or expected location(s) may be based on a fundamental assumption of motion within the stream, e.g., constant velocity and/or constant acceleration. In some instances, characterization of motion-related errors may result in a more accurate model of the micro-entity motion that accounts for various types of motion-related error. Characterization and compensation of motion-related errors of micro-entities can be useful for diagnosing and improving the performance of apparatus designed to measure and/or operate on micro-entities moving in streams.

In one example, techniques and apparatus are developed to characterize and compensate motion-related error for a flow cytometer. Deviations in interrogation-point arrival times of micro-entities moving in a flow cytometer stream are found to be stably and functionally dependent upon a value measured with respect to a system parameter. A model of the functional dependence of the deviations can be used to reduce measurement errors and improve operation (e.g., cell throughput and/or sort purity) of the flow cytometer.

According to some embodiments, a system for compensating motion-related error associated with micro-entities that move between a first location and at least a second location comprises detection apparatus configured to generate a first signal when a micro-entity crosses the first location and to generate at least a second signal when the micro-entity crosses at least the second location. The first location may be before the second location in a stream, or may be after the second location in the stream. The system may include one or more processors configured to receive at least the first signal, and determine from the first signal a value with respect to a parameter of the system. The value may be determined for each micro-entity crossing the first location. As an example, the value may be a time or phase offset between an arrival of a micro-entity at the first location measured with respect to a system metric, e.g., a system clock or periodic signal. The one or more processors of the system may be further configured to adjust, by a correction amount that compensates for motion-related error associated with the micro-entity, an observation or operation time for observing or operating on the micro-entity at the second location. The correction amount may be determined from an error model that predicts the motion-related error associated with the micro-entity from the value determined with respect to the system parameter. Correction amounts may be determined and used to adjust measurement or observation times at additional locations along a path through which the micro-entities move.

In some embodiments, a system for compensating motion-related error associated with moving micro-entities comprises a source of periodic energy, e.g., a transducer, configured to couple the periodic energy to a stream of moving micro-entities. The value that is determined with respect to a parameter of the system may comprise a time or phase offset measured with respect to a feature of a driving signal provided to the periodic energy source. The system may further include lasers or sources of focused radiation that are used to optically probe the moving micro-entities at one or more locations along the stream. The system may further include optical detectors configured to detect radiation from the optically-probed micro-entities.

Related methods for compensating motion-related errors of micro-entities moving in a stream are also contemplated. For example and according to one embodiment, a method for compensating motion-related errors associated with micro-entities that move in a system between a first location and at least a second location may comprise detecting, with detection apparatus, a signal indicating a presence of a first micro-entity at the first location. The method may further include an act of determining, from the signal for the first micro-entity with at least one processor, a value with respect to a parameter of the system. Additionally, the method may include adjusting, with the at least one processor by a correction amount that compensates for motion-related error associated with the first micro-entity, an observation or operation time for observing or operating on the first micro-entity at the second location. The correction amount may be determined from an error model that predicts the motion-related error associated with the first micro-entity from the value determined with respect to a parameter of the system.

Also contemplated as being within the scope of the invention is tangible, manufactured computer-readable medium and/or storage devices that include machine-readable instructions that, when executed by at least one processor, adapt the at least one processor to execute one or more acts of methods for characterizing and/or compensating motion-related errors of micro-entities moving in streams. The computer-readable media and/or storage devices may be used to adapt instruments that are designed to measure and/or operate on micro-entities that move in streams.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

DETAILED DESCRIPTION

As described above, in some applications involving moving micro-entities, it may be desirable to predict or know an arrival time of a micro-entity at a pre-selected location, or conversely to predict or know a location of the micro-entity at a selected time. For low-accuracy and/or low-speed systems, predictions based on fundamental assumptions (e.g., average velocity $v_{avg}$ of the entities within the stream, or average transit times $\Delta t_{avg}$, constant velocity, constant acceleration) may be sufficient for obtaining reasonably accurate predictions of a micro-entity arrival time or its location for purposes of measurements or operations on the micro-entity. However, for high-accuracy and/or high velocity systems, higher-order motion characteristics of the micro-entities within the stream may lead to unacceptably large uncertainties or errors in arrival times or locations of the entities within the stream. Large uncertainties can limit the ability to operate on the moving micro-entities and/or collect data representative of the moving micro-entities. As a result, large uncertainties in time or location can impose limits on the speed, accuracy, and performance of the system.

According to some embodiments, motion-related errors of micro-entities that move in a system between a first location and at least a second location can be characterized and compensated. In some systems, motion-related error may exhibit a functional and/or stable dependence on a value for a moving micro-entity that is measured with respect to a parameter of the system. Measurements of the moving micro-entities may be made to characterize the motion-related errors and reveal a dependence of the error on the system parameter. From such characterization measurements, a model of motion-related error may be constructed and used to predict and/or compensate motion-related errors of micro-entities moving in the system.

Figure 1:
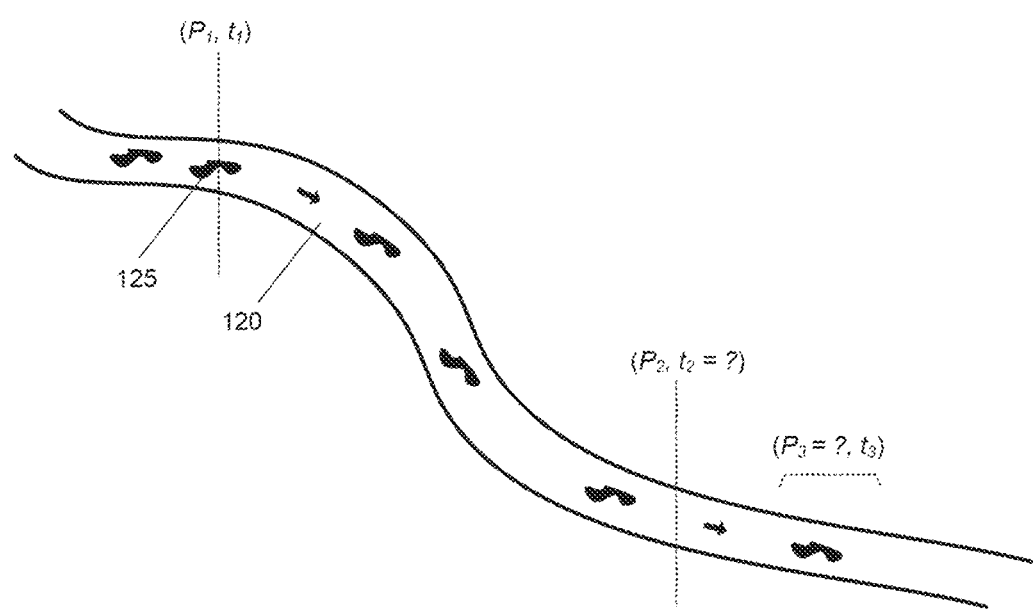
FIG. 1 depicts a stream of moving micro-entities.
Figure 2:
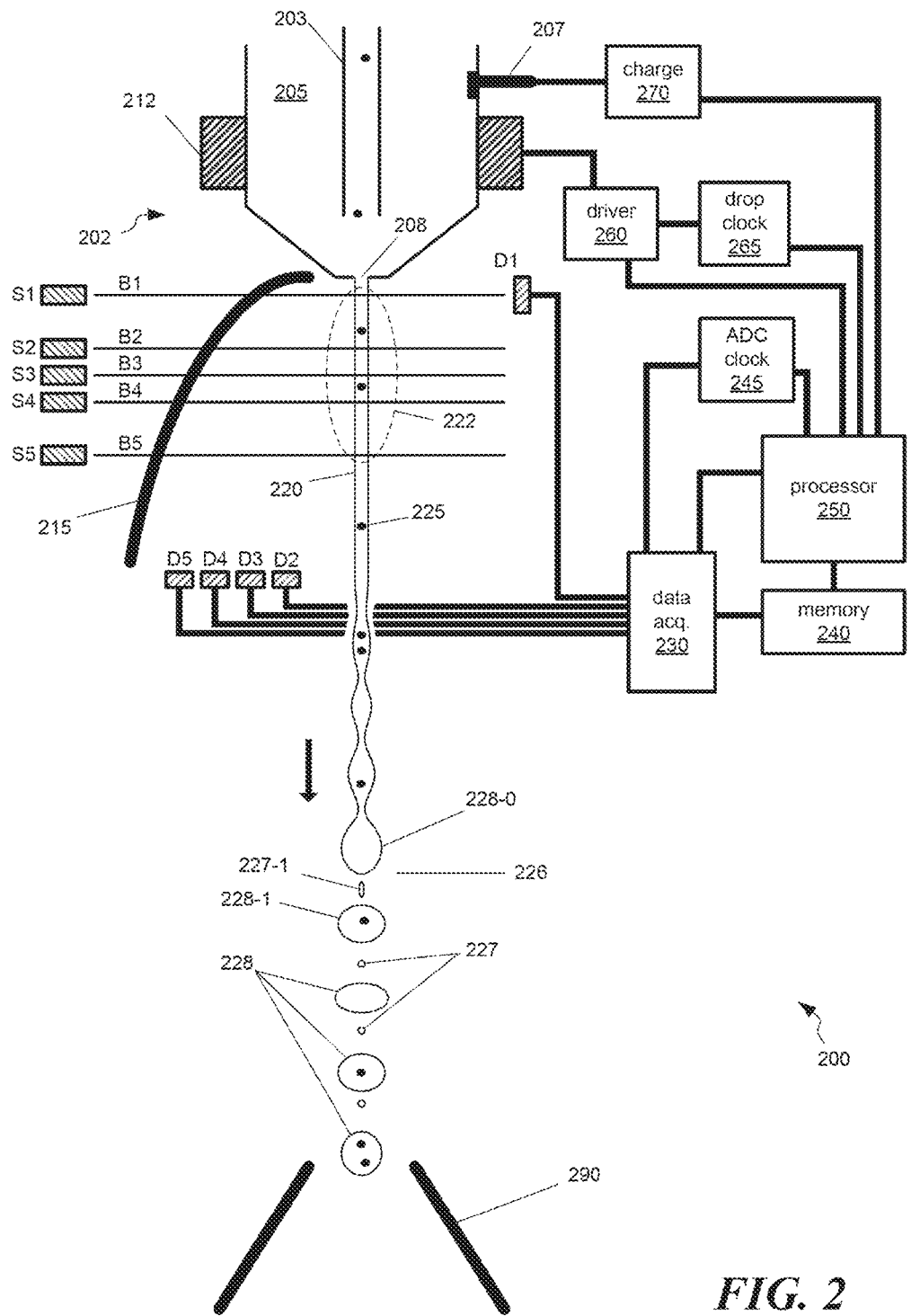
FIG. 2 schematically depicts selected components of a flow cytometer, according to one embodiment.

FIG. 2 schematically depicts certain elements of a flow cytometer 200. A flow cytometer is one example of a system that includes a stream of moving micro-entities 225 (typically cells moving in single file). Although embodiments of the invention will be described primarily in connection with a flow cytometer, equivalent techniques and apparatus may be used in other systems or instruments that utilize streams of moving micro-entities. For example, embodiments of the invention may be implemented in microfluidic systems and micro- or nano-fabrication systems in which micro- or nano-entities are fabricated in fluidic streams. The various systems may be adapted to perform one or more operations on the moving micro-entities. Types of operations in these systems may include any combination of the following operations: measuring a characteristic of the micro-entity, imaging, illuminating to detect fluorescence, sorting, transforming (e.g., introducing a chemical or electrical charge, illuminating to cross-link a polymer, illuminating to transform a component of the micro-entity), size analysis, and weight analysis.

I. OVERVIEW OF A FLOW CYTOMETER SYSTEM

Flow-cytometry-based cell sorting was first introduced to the research community more than 30 years ago. It is a technology that has been widely applied in many areas of life science research, serving as a highly useful tool for those working in fields such as genetics, immunology, molecular biology and environmental science. Unlike bulk cell separation techniques such as immuno-panning or magnetic column separation, flow-cytometry-based cell sorting instruments measure, classify and then sort individual micro-entities serially at rates of several thousand cells per second and higher. This rapid "one-by-one" processing of single cells has made flow cytometry a valuable tool for extracting highly pure sub-populations of cells from otherwise heterogeneous cell suspensions.

Cells targeted for sorting are usually labeled in some manner with a fluorescent material. The fluorescent probes bound to a cell fluoresce as the cell passes through a tightly focused, high intensity, light beam (typically a laser beam). A computer records emission intensities for each cell. These data are then used to classify each cell for specific sorting operations. Flow-cytometry-based cell sorting has been successfully applied to many cell types, cell constituents and microorganisms, as well as many types of inorganic particles of comparable size.

There are two basic types of cell sorters in current use. They are the "droplet cell sorter" and the "fluid switching cell sorter." The droplet cell sorter utilizes micro-droplets as containers to transport or convey selected cells to a collection vessel. The micro-droplets are formed by coupling ultrasonic energy to a jetting stream. Droplets containing selected cells are then electrostatically steered to a desired location to sort the selected cells from a larger population. This can be a very efficient process, allowing as many as 90,000 cells per second to be sorted from a single stream.

The second type of flow cytometry-based cell sorter is the fluid switching cell sorter. Some fluid switching cell sorters utilize a piezoelectric device to drive a mechanical system which diverts a segment of the flowing sample stream into a collection vessel. Compared to droplet cell sorters, fluid switching cell sorters can have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits some fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

Recently, microfluidic sorters have been developed that utilize MEMS actuators or electric fields to divert micro-entities as needed. These sorters may sort within a completely enclosed chip, such as a microfluidic chip. The use of microfluidics can enable many parallel sorts to occur from a same input channel and enhance the net throughput in microfluidic sorters.

With reference to FIG. 2, a flow cytometer 200 may comprise a nozzle 202 from which a fluidic stream 220 issues. The nozzle 202 may include a first chamber 205 that contains a sheath fluid. The nozzle may also include a conduit 203 that conveys a sample fluid to a core of the stream 220. Micro-entities 225 may be in suspension in the sample fluid. The sheath fluid and sample fluid may flow toward a nozzle orifice 208 and exit from the nozzle 202 in the stream 220. The sheath fluid may form a sheath around the periphery of the stream.

The nozzle 202 may further include a transducer 212 configured to couple energy into at least the sheath fluid. The transducer 212 may be an acoustic transducer that couples acoustic energy into the sheath fluid on a regular periodic basis. The coupling of periodic energy into the sheath and/or sample fluids can regulate, with high uniformity, the formation of droplets 228 in the stream 220 issuing from the nozzle 202. Perturbations in the stream 220 result from acoustic energy that is coupled to the fluid inside the nozzle (e.g., from a periodic vibration of a piezoelectric transducer in the nozzle). Droplets 228 form, due to surface tension as predicted by Rayleigh, at the acoustic frequency. Within an acceptable range of parameters (frequency, sheath pressure, transducer drive amplitude, etc.) droplets break free at a uniform distance from the nozzle. In some embodiments, a cell sorter may implement a feedback system that keeps the break-off position 226 at an approximately constant distance from the nozzle orifice 208. Satellite droplets 227 may also form along with the droplets 228.

As depicted in FIG. 2, the jet exiting the nozzle of a droplet cell sorter carries the micro-entities 225 for several millimeters down the stream 220 until they are encased in one of the micro-droplets 228 that synchronously break away from the stream. The micro-entities may move at approximately a constant velocity along the stream, in some embodiments. In some droplet cell sorters, the time of flight ($t_f$) from a measurement point (e.g., the first interrogation point at beam B1) to where the cell passes through the break-off point 226, where the stream breaks into a free droplet, is constant to within about 1% of the droplet generation period.

The formation of droplets 228 may be affected by a drop-drive frequency $f_d$ and amplitude $A_d$ of a signal applied to transducer 212. In some embodiments, the drop-drive frequency $f_d$ may be adjusted by a drop clock 265, which in turn may be controlled by a processor 250 of the system. The drop-drive amplitude $A_d$ may be adjusted by a driver 260 configured to provide a drive signal to transducer 212. In some embodiments, the driver 260 may receive an amplitude control signal from processor 250. According to some embodiments, increasing the drop-drive amplitude $A_d$ moves the droplet break-off point 226 toward the nozzle. Changing the drive frequency $f_d$ changes the frequency at which droplets are produced. In some embodiments, a drive frequency may be selected to have any value between about 10 kHz and about 250 kHz.

The processor 250 may be any type and form of data processing device, e.g., a microprocessor, microcontroller, a computer connected to the system, or a field-programmable gate array (FPGA). There may be more than one processor in the system in some embodiments. In some cases, there may be a combination of processor types, e.g., a microprocessor and one or more FPGAs.

The system 200 may also include apparatus for placing a charge on each droplet 228. Charging of droplets may be used for sorting operations of the individual droplets, and thereby sorting of the micro-entities contained in the droplet. A charge source 270 may be controlled by the processor 250 to apply a selected electric potential value for a selected amount of time to a conductive probe 207 that is in electrical contact with the sheath fluid and/or sample fluid. For example, as a last attached droplet 228-0 is forming in the stream 220, a first electric potential may be applied to conductive probe 207. Since the fluids are conductive, the surface of the fluid charges and the last attached droplet acquires an electric charge. When the last attached droplet breaks from the stream to form a droplet, e.g., moves to the position of the preceding droplet 228-1, the newly formed droplet retains a charge that is dependent on the electric potential applied to the fluid and stream at the time the last attached droplet 228-0 broke free of the stream 220. In some cases, the charge on the newly formed droplet is proportional to the square root of the electric potential applied to the fluid. After the last attached droplet breaks free, a second electric potential may be applied to the conductive probe 207, so that the next droplet that forms as the last attached droplet will acquire a charge different from, or same as, its predecessor. In some instances, no charge (e.g., a ground potential or neutral charge) may be applied to a droplet.

The system 200 may also include apparatus for sorting the droplets, and thereby sort any micro-entities that are conveyed by the droplets. The sorting apparatus may include electrostatic deflection plates 290 to which an electric potential is applied so as to establish an electric field between the plates. As a charged droplet traverses the electric field, the droplet may be deflected laterally and collected in a sample container (not shown). Droplets that are given a neutral charge may travel between the deflection plates 290 without being deflected by the plates. In this or a similar manner, micro-entities may be sorted.

In various embodiments, the system 200 may include components configured for detection operations, e.g., to detect one or more signals that may be used to characterize the moving micro-entities. The one or more signals may be used in making a decision about a subsequent operation, e.g., a sorting operation, performed on a stream segment containing the micro-entity. For the embodiment depicted in FIG. 2, the detection operations may include illuminating the micro-entities with optical radiation from one or more radiation sources S1, S2, . . . S5. The radiation sources may emit beams of radiation B1, B2, . . . B5 at different wavelengths. In some embodiments, one or more sources may emit radiation at a same wavelength. The radiation sources S1, S2, . . . S5 may be laser sources in some embodiments, high-intensity arc-lamp sources in some embodiments, high-intensity light-emitting diodes in some embodiments, or any suitable radiation source. The beams of radiation may be separated and arranged to intersect the stream 220 near the nozzle 202. In some embodiments, the beams may be focused onto the stream 220. The beams of radiation B1, B2, . . . B5 may interact with the micro-entities to generate scattered radiation or excite fluorescent radiation. The scattered or fluorescent radiation may be detected, e.g., with a detector D1, which may generate an electrical signal representative of the detected radiation. One or more signals representative of fluorescent radiation may be detected, e.g., with one or more detectors D2, D3, . . . D5.

Fluorescent radiation and/or scattered radiation from the micro-entities may be collected with an optical element 215 and directed to the detectors.

In some flow cytometers and other systems, e.g., microfluidic systems, other types of particle detection and sensing may be employed. In some embodiments, direct electrical sensing or Coulter-type measurements may be made of the micro-entities moving along the stream. In some cases, Coulter volume measurements may be made to characterize the micro-entities. In some implementations, other types of sensing may be employed, e.g., magnetic, magneto-optic, electro-optic, thermal. Signals or measurements made using any of these detection and sensing techniques may be used to characterize and/or compensate for motion-related errors of the micro-entities. For example, a signal or measurement obtained using one or more of these detection and sensing techniques may be used to develop a model of motion-related error for the micro-entities, and subsequent signals or measurements may be used to determine correction amounts that compensate for the motion-related error.

A droplet cell sorter may be configured to operate as a sense-in-air (SIA) instrument. In such a system, at least one excitation laser beam is focused onto the stream 220 comprising a flowing sheath stream and an inner core stream conveying micro-entities (aligned in single file). The stream is positioned such that this intersection occurs at the focus of one or more light collection systems. The point of common foci is often referred to as the interrogation point. There may be multiple laser systems and multiple interrogation points spatially separated along the stream 220, as depicted in FIG. 2. Each of these interrogation points may have one or more separate laser beams and signal detection apparatus. The interrogation points may be limited spatially to an interrogation region 222 near the nozzle 202. Spatial filtering may be used to reduce an observation region (also referred to as a field of view (FOV)) associated with a single interrogation point and to mitigate cross-detection of nearby interrogation points. A FOV for a single interrogation point may be on the order of 50 microns. Therefore, careful and precise alignment of the stream, laser focus, and optical system's focus may be required. In some implementations, the observation region associated with a single interrogation point may be limited to a few tens of microns. As a micro-entity travels down the stream, it passes sequentially through each interrogation point. Radiation from the micro-entity may be measured and recorded from each interrogation point. These measurements may be correlated prior to separation from the stream of the segment containing the micro-entity. The charged drop may then travel through air to the electrostatic plates 290 where they will be deflected for sorting purposes.

Though five probing beams and five detectors are shown in FIG. 2, fewer or more probing beams and fewer or more detectors may be used in some systems. In some implementations, there may be more than one detector for a probing beam, and optical components may divide and direct optical emission to more than one detector. In some cases, optical and/or spatial filtering may be used in the detection optics to separate fluorescent signals and/or block radiation from the radiation sources. One example of a flow cytometer that utilizes five optical sources to probe the micro-entities is the sy3200™ flow cytometer (available from iCyt Mission Technology of Champaign, Ill.).

Time-varying signals from the detectors D1, D2, D3, . . . D5 may be collected, e.g., digitally sampled with data acquisition hardware 230 that may be clocked by an analog-to-digital converter clock 245, and stored in memory 240 for subsequent analysis by processor 250. In some embodiments, the data may be provided directly to processor 250 for analysis. In some implementations, the data is stored temporarily in memory 240, e.g., in a buffer or a suitable random access device, and then read out by the processor 250 for analysis.

As may be appreciated from the description of the flow cytometer above, the data signals from the detectors may be pulses representative of the micro-entities 225 that traverse the beams of radiation B1, B2, . . . B5. Each pulse may have a peak height, width, and area. The pulse heights, widths, and areas may be evaluated by processor 250 and used to characterize each micro-entity 225. The evaluated characteristics may then be used to make a decision about a subsequent operation on each micro-entity 225 or droplet that contains one or more micro-entities.

Although the droplets 228 may be formed at periodic intervals, the micro-entities 225 may be dispersed in the stream 220 at random intervals. For example, the micro-entities may be in a dilute suspension in the sample fluid, which is fed to the nozzle 202. The micro-entities may then arrive at random times at the nozzle's orifice 208. As a result and as depicted in FIG. 2, some droplets may not contain a micro-entity and some may contain more than one micro-entity, e.g., doublets, triplets, or more.

Proper operation of a cell sorter requires that measurement data recorded from each interrogation point be correctly correlated for each micro-entity that generated the data. To correctly characterize a selected micro-entity in a stream 220, it is necessary to know what signals from the detectors D1, D2, D3, . . . D5 correspond to the selected micro-entity. To correctly perform an operation (e.g., sorting) on the selected micro-entity when encased in a droplet, it is necessary to further know in which droplet 228 that micro-entity will be encased. For example, it is necessary to properly assign each detected signal to a same micro-entity (and droplet that will contain the micro-entity) from which the detected signals were produced, so that an accurate characterization of that micro-entity can be determined. Additionally and for sorting purposes in the flow cytometer example, it is necessary to know when the micro-entity will arrive at the last attached droplet 228-0 in order to apply a correct electrical potential to the conductive probe 207 at the correct time, so as to impart a desired charge to the droplet 228-0 that contains the micro-entity. When properly charged, the last attached droplet will subsequently detach as a free droplet and be sorted according to its charge.

As an aid in understanding aspects of the invention as implemented in a flow cytometer, details of data handling, timing of operations, and calibration methodologies for a sort-in-air flow cytometer will now be described. However, the described techniques and apparatus are applicable to systems other than flow cytometers in which micro-entities are moved from at least a first location to one or more second locations and in which operations may be performed on the moving micro-entities.

II. CALIBRATION

Figure 3A:
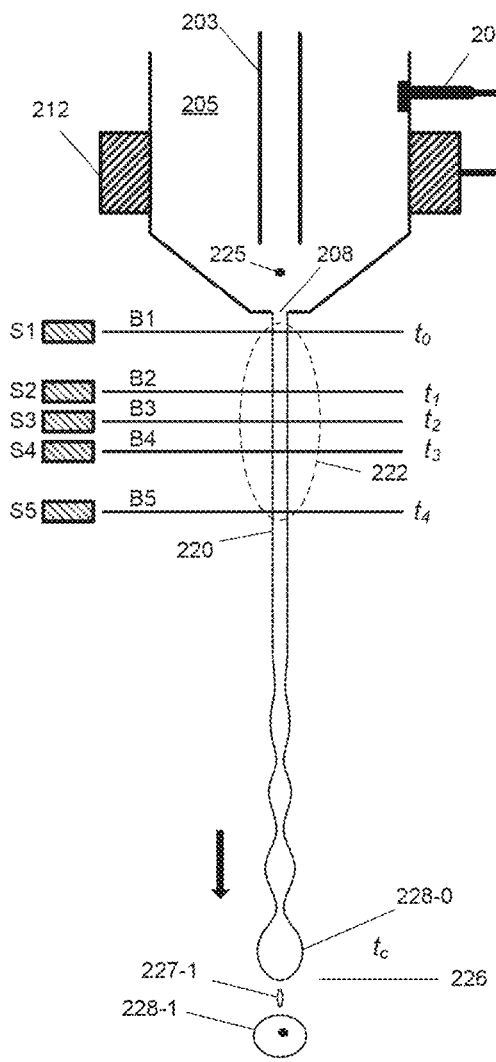
FIG. 3A schematically depicts selected components of a flow cytometer for purposes of explaining calibration of droplet dynamics.

Data handling and timing of system operations for a system in which micro-entities move from a first location to one or more additional locations may be established in calibration trials using calibration particles. As one example, a droplet cell sorter may be calibrated so that the data acquisition system can associate data collected for each cell or micro-entity with the specific drop that will carry it (and possibly other micro-entities) away from the stream and into a collection vessel. Calibration trials or runs may be executed at a manufacturing facility to initially set up the system and/or they may be run on a routine basis, e.g., prior to each experiment, to verify operation of the system. The calibration may be accomplished through empirical observation using highly fluorescent micro-entities. The sort outcome may be observed by sorting drops on to a microscope slide for manual viewing or by using an automated detection system to record emission from droplets. According to some embodiments, the micro-entities used for calibration purposes may comprise calibration beads, e.g., fluorophore-tagged polystyrene micro-beads. In some embodiments, fluorescent cells may be used for calibration purposes. The calibration beads may be diluted in the sample fluid to an extent that there may be two or fewer beads in the stream 220 issuing from the nozzle 202 at any given instant in time, as depicted in FIG. 3A for example.

As a micro-entity 225 or calibration bead travels along the stream 220, it crosses the interrogation beams B1, B2, . . . B5 that are present in the stream, and is later encapsulated by a droplet 228-1 that has broken free from the stream. For a multi-interrogation point system, it is necessary to correlate multiple measurements (e.g., signals as depicted in FIGS. 3B-3F) made for a single micro-entity as it passes sequentially through each interrogation point. The correlated data are used to make sort decisions for each micro-entity, and affect the sorting of droplets that contain the micro-entities.

The correct identification of signals from multiple interrogation points as being associated with a single micro-entity and droplet may be determined in calibrations runs. By running calibration micro-entities through the system, the data acquisition system may be configured such that a passing of a single micro-entity through a selected "trigger" interrogation point (e.g., a first interrogation point having a beam B1) triggers a timing sequence that "opens" or selects narrow data acquisition windows (e.g., selects segments of data streams from each of the interrogation points) precisely as the micro-entity is expected to arrive at each of the other interrogation points. To improve system throughput (important for a cell sorter), these timing windows should be kept as short in duration as possible.

In modern digital data acquisition systems, it is common to buffer the analog-to-digital converter (ADC) samples for measurement data from all interrogation points. In some cases, the data is buffered long enough to allow triggering to occur from downstream interrogation points, rather than relying only on triggering from a first interrogation point along the stream. Stated alternatively, when data is buffered, a trigger interrogation point may be a point at which a trigger signal is generated after one or more signals for a micro-entity have been generated at other interrogation points. Consequently, a selected "trigger" interrogation point may be any one of the interrogation points in the system.

According to some embodiments, the beam crossing times and arrival at the last attached drop may be estimated from a calculation based on the crossing event of the first beam B1, if one were to know the velocity of the stream and the distances to each interrogation point in the stream and the distance to the pinch-off point 226. However, in some systems the distances may vary from day-to-day or run-to-run operation, and there may not be a convenient way to measure the distances or fluid velocity directly.

Figure 3B:
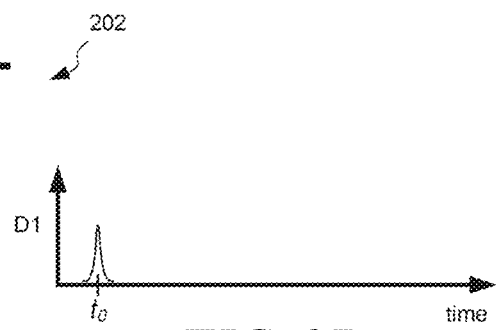
FIGS. 3B-3G depict graphs of signals that may be used to indicate the presence of a micro-entity at a respective interrogation point or to characterize a micro-entity; according to some embodiments.
Figure 3C:
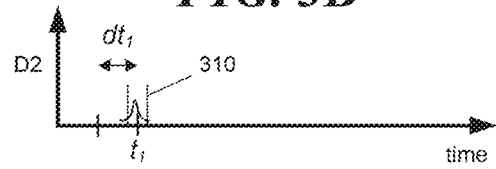
Figure 3D:
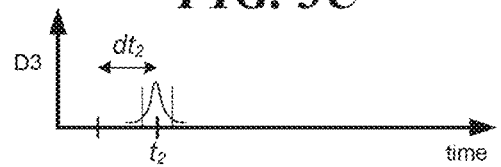

In some embodiments, effective transit times to the beam crossings and pinch-off point may be determined by calibration runs. As an example, a fluorescent calibration bead crossing the first beam B1 may generate a fluorescent signal at time $t_0$ as depicted in FIG. 3B. In some embodiments, this signal may be used as a "trigger" signal that identifies to the system the arrival of a new micro-entity to be analyzed and subsequently processed (e.g., sorted). In other embodiments and as noted above, another interrogation point may be used to provide a trigger signal rather than the first interrogation point. Along with and corresponding to the trigger signal, a series of signals or events occurring at approximate times $t_1$, $t_2$, $t_3$, $t_4$, $t_c$ may be generated by the same micro-entity responsible for the trigger signal, as depicted in FIGS. 3C-3G.

By running a number of calibration beads through the system, the average time offsets or transit times $dt_1$, $dt_2$, $dt_3$, $dt_4$, $dt_c$ that occur between signals and/or events can be determined. When these times are known, it is then possible to determine which signals are to be associated with a micro-entity that initiated a trigger event. For example, the correct signals appear in the other detector data streams at times $dt_1$, $dt_2$, $dt_3$, $dt_4$ spaced from the trigger event at time $t_0$. It is further possible to determine, after processing the signals, what charge value to apply to a droplet that will contain that micro-entity. In some embodiments, signals from other micro-entities in or near the segment of the stream carrying a micro-entity of interest may be processed to determine what charge will be applied to a droplet formed from the stream segment. When the time offsets are known, the system may be run with useful samples that are to be analyzed and processed instead of the calibration beads.

Figure 3E:
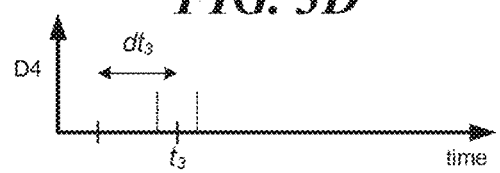
Figure 3F:
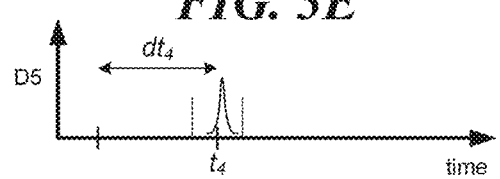
Figure 3G:
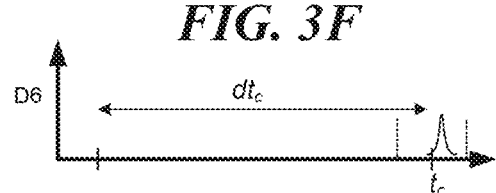

In some embodiments, additional signals, e.g., pulses at times $t_1$, $t_2$, $t_3$, $t_4$, may or may not be generated as the same micro-entity crosses the other interrogation beams B2, B3, B4, B5. A signal may not be produced at an interrogation point, e.g., as depicted in FIG. 3E, if a fluorescent micro-entity is not responsive to an excitation radiation at the interrogation point. A signal may be generated as the micro-entity arrives at the last attached drop 228-0 at time $t_c$. According to some embodiments, the micro-entity may be imaged as it arrives at the last attached drop 228-0 and at the time of charging of the last attached drop via stroboscopic excitation.

Since the signals from interrogation points may be digitally sampled and recorded, a signal from an interrogation point may be represented by a set of digital samples within a digital data stream, e.g., a data stream from an analog-to-digital converter. Accordingly, the calibration procedure may identify what data stream segment, or observation window, in a data stream from detection apparatus for an interrogation point corresponds to a micro-entity that initiated a trigger event upon crossing a trigger interrogation point. The calibration procedure may configure the data acquisition system to identify timing or locations of data segments in the data streams from each interrogation point that are associated with a same micro-entity. In some embodiments, time stamps associated with the generated data from each detector may be used to aid in identifying pulses that belong to each micro-entity.

As may be appreciated from the above discussion, there are two problems to be solved by the system 200 upon the occurrence of a trigger pulse. The first problem pertains to identifying what signals from the other detector data streams are generated by the same micro-entity that generated the trigger pulse. As noted above, the correct signals or data stream segments in other detector data streams can be identified from the time offsets $dt_1$, $dt_2$, $dt_3$, $dt_4$ derived from the calibration runs, or using other suitable internal correlations. When the signals or data stream segments are correctly identified, the micro-entity may be characterized properly for a subsequent operation such as sorting.

The second problem pertains to droplet membership or determining what droplet the micro-entity will end up in, so that a correct charge may be applied to that droplet. The second problem is somewhat particular to a droplet cell sorter, but may be pertinent to any system that forms regularly-spaced capsules that convey micro-entities. For example, the second problem may pertain to a microfluidic system in which alternating types of immiscible fluids are introduced into a channel, or in which bubbles of air are periodically introduced into a channel to form separated capsules of fluid. In such systems, the formation of droplets or capsules may be on a periodic basis, and the arrival of micro-entities into the stream may be on a random basis.

Figure 4A:
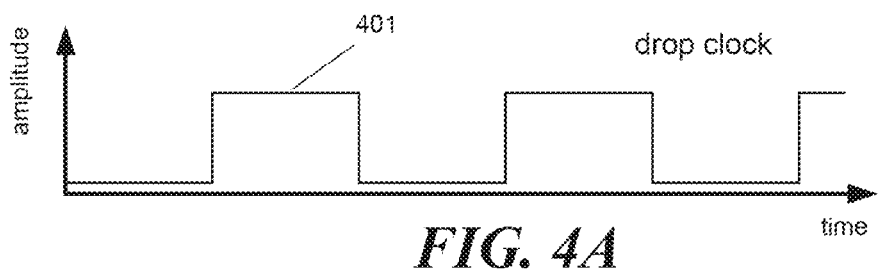
FIGS. 4A-4F are plots depicting various system signals and data that may be used or observed in a flow cytometer, according to some embodiments.
Figure 4B:
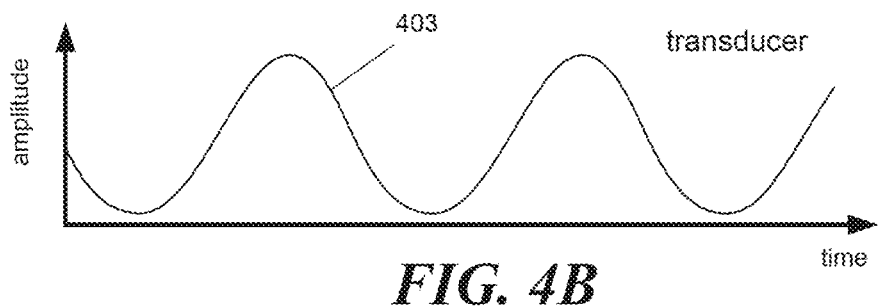
Figure 4C:
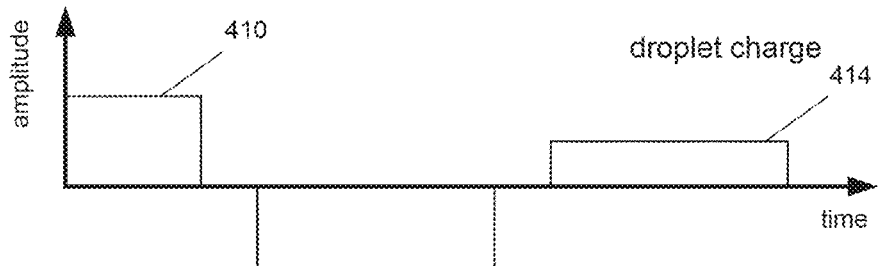

In further detail with regard to the formation of droplets and determining droplet membership, a drop clock signal 401 depicted in FIG. 4A may be used to generate a periodic transducer signal 403 (FIG. 4B) that is applied to the transducer 212 in the flow cytometer nozzle 202. As described above, the transducer 212 imparts acoustic energy to fluid in the nozzle and stream 220. Additionally, charging pulses (depicted in FIG. 4C) may be applied to the conductive probe 207, so as to charge the last attached drop 228-0. The transducer signal may be synchronized or phase-locked to the drop clock signal. The amplitude of the transducer signal may be adjusted to move the break-off point 226 to a selected location or distance from the nozzle 202. The charging pulses may be phase locked to the drop clock and may or may not be in phase with the drop clock and/or transducer signal. According to some embodiments, there is no variable phase adjustment that is used to adjust a phase between the charging pulses and transducer signal and/or drop clock in an experimental or calibration run of the system 200.

According to some embodiments, the drive amplitude to the transducer is adjusted to produce clean sort streams when different sort charge pulses are applied to the last attached drop. With the transducer signal amplitude set to produce clean sort streams and the break-off point 226 maintained at an approximately fixed distance from the nozzle 202, fluorescent calibration beads or micro-entities may be run through the system to determine droplet membership. In some calibration runs, calibration entities can be fed through the system at a low rate, so that there will be no confusion of data signals. By detecting the calibration entities in the pinch-off region, a determination can be made as to which signals from the interrogation points for a particular micro-entity correspond to a droplet formation and/or droplet charging time at the pinch-off region. In some implementations, this determination may amount to finding a value for $dt_c$. Once the determination is made, membership of a micro-entity's signals to a particular droplet can be assigned.

With droplet membership determined, sorting decisions for one or more micro-entities within a droplet can be made. Sorting decisions can be made based upon correlations of signals for the one or more micro-entities that will be within the droplet. The physical act of sorting can be implemented by assigning a droplet charge value to the droplet. For example a droplet charge value 412 may be assigned to the droplet. In some embodiments, charge values applied to the droplets may be quasi-discrete. For example, the charge values may be separated by first amounts corresponding to the discrete sort streams, although a final charge amount may be adjusted to account for higher-order effects, e.g., capacitive coupling to adjacent droplets.

In some embodiments, the average time offsets $dt_1$, $dt_2$, $dt_3$, $dt_4$, $dt_c$ that are found in calibration runs may be computed in terms of system clock cycles, e.g., in terms of drop clock cycles (FIG. 4A) or analog-to-digital (ADC) clock cycles (FIG. 4D) or a combination of both clock cycles. A high resolution of the offsets may be obtained by using a system clock that operates at a higher frequency than other clocks. In a flow cytometer, an ADC clock may run at 10's or 100's of MHz, whereas a drop clock may run at frequencies several orders of magnitudes slower than these values. A delay value computed in terms of ADC clock cycles will provide a higher resolution. In some implementations, long delays may be calculated in terms of slower clock cycles, e.g., drop clock cycles. In some cases, long delay may be calculated in terms of a mix of slower and faster clock cycles. For example, if the period of the drop clock is $T_d$ and the period of the ADC clock is $T_{ADC}$, then a delay may be calculated as $$dt = NT_d + aT_d \quad (1)$$

where N is an integer and a represents a fraction: $0 < a < 1$. The value a may be computed as $$a = MT_{ADC}/T_d \quad (2)$$

where M is an integer. Combining EQS. 1-2 yields $dt = NT\_d + MT\_ADC$.

III. DATA ACQUISITION

As noted above, the time offsets or delays $dt_1$, $dt_2$, $dt_3$, $dt_4$ can be used to select the appropriate times for observation timing windows 310 or data stream segments in which a signal from the micro-entity is expected to appear for each interrogation point and for a same micro-entity that has initiated a trigger event (e.g., crossing of trigger interrogation point at B1). Data appearing within the observation windows would be ascribed to that micro-entity and processed to make a decision about an operation (e.g., a sorting operation) on that micro-entity. As noted above, since data from the interrogation points may be buffered, any interrogation point may serve as a trigger point and the observations windows for a single micro-entity may occur before and after a trigger signal.

Figure 4D:
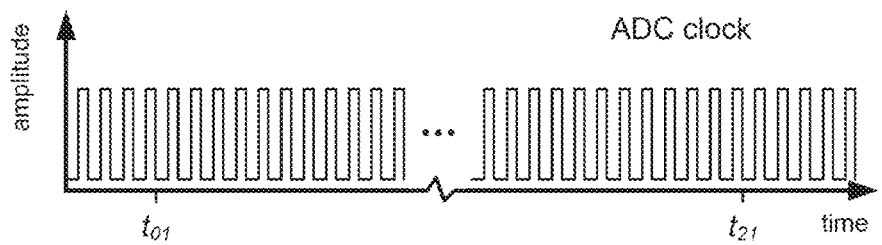
Figure 4E:
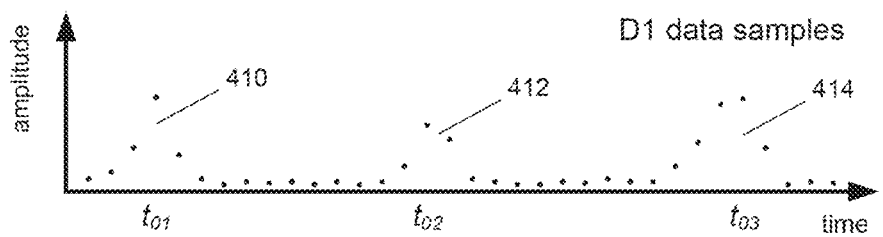
Figure 4F:
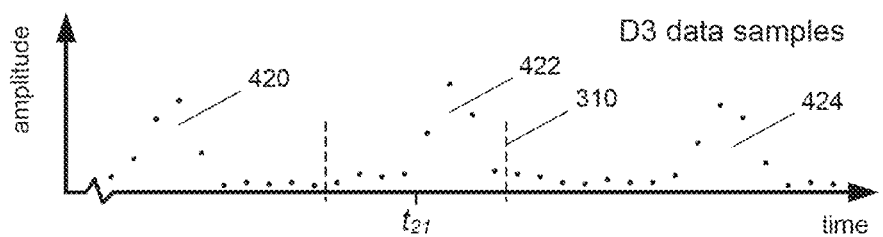

In some embodiments, the observation windows 310 identify time segments in data streams from the detectors D1, D2, ... D5 at which a signal is to be attributed to a particular micro-entity. For example, each of the detectors D1, D2, ... D5 in the system may output a stream of data comprising samples of signals produced by micro-entities crossing a respective interrogation beam B1, B2, ... B5. The samples may be acquired at a high data rate according to an analog-to-digital converter clock, e.g. as depicted in FIGS. 4D-4F. A micro-entity crossing a selected beam that will be used as a trigger (beam B1 in this example), will generate a trigger signal (e.g., a pulse) that can be detected and used to identify an arrival time of that micro-entity at the trigger interrogation point. In the following illustrative example, a feature of the trigger signal used to mark arrival time or a reference time t01 is taken to be a peak of the trigger pulse, but other values may be used in other embodiments, e.g., a rising edge threshold level selected by a system user, a threshold value of an integral of the pulse. The reference time $t_{01}$ of the trigger event may be associated with a clock cycle, as depicted in FIG. 4D.

With the reference time $t_{01}$ established for the micro-entity and a delay (e.g., delay $dt_2$) known from a calibration run, it can be determined, in terms of clock cycles or data samples, where to look in a data stream for a subsequent event (e.g., crossing of beam B3) for the same micro-entity that moves through the system. For example and with reference to FIGS. 4D-4F, a first micro-entity may cross a trigger beam (taken as beam B1 in this example), and generate a trigger pulse 410 at time $t_{01}$. The trigger pulse 410 may be detected in a stream of data from detector D1. The stream of data may include subsequent trigger pulses 412, 414 for other micro-entities. By knowing the delay time $dt_2$, a subsequent signal generated by the first micro-entity as it crosses beam B3 can be found in a data stream from detector D3. The subsequent signal would appear in an observation window 310 that straddles an expected arrival time $t_{21}$ of the micro-entity at beam B3. The observation window would be offset from the trigger event $t_{01}$ by a number of clock cycles (e.g., ADC clock cycles in this example) that correspond to the delay time $dt_2$. In this observation window 310, a pulse 422 appears to arrive late, as depicted in FIG. 4F. Other pulses corresponding to other micro-entities also appear in the trace of FIG. 4F.

Data received from the detectors D1, D2, . . . D5 may be stored in temporary data storage, e.g., a FIFO buffer. In some embodiments, the data may be stored in long-term data storage. Since the data is stored, there is greater flexibility in handling and processing the data because it need not be processed in real time. For example, with data storage, it is possible to look backwards and forward in time from a selected event. According to some embodiments, the aspects of determining locations of observation windows according to clock cycles can be transformed to determining locations of data signals according to memory address or memory location (e.g., provided the data is stored sequentially in address space or stored in association with an observation time). Delay values in time, e.g., $dt_2$, can be transformed to offsets in address space.

In such implementations, any of the beam-crossing events in the stream 220 may be used as a reference trigger event for a particular micro-entity. For example, a signal detected for a micro-entity crossing a second beam B2 in the stream may be used as a trigger event. Corresponding data for other beam crossings for the same micro-entity may be found by looking forward and backward in address space by address offsets corresponding to the appropriate delay times.

Determining the timing or locations of the data acquisition observation windows 310 assures that signals, which may include the absence of a signal, are recorded correctly for each micro-entity that traverses the system. As depicted in FIG. 3E some micro-entities may not generate a signal at an interrogation point, e.g., provide no measurable signal over a background level. For example, some micro-entities in a sample may be labeled with a fluorescent tag that is sensitive to some interrogation beams and not sensitive to other interrogation beams. The absence of a recognizable signal above a background noise level can be important in classifying or characterizing the micro-entity. Therefore, a correct determination of an observation window 310 can aid in confirming the absence of a signal for a micro-entity at that interrogation point or beam crossing.

IV. MOTION-RELATED ERROR

In systems having streams with moving micro-entities, such as a flow cytometer, the micro-entities 225 may arrive at the interrogation points along the stream with deviations from expected arrival times. For example, even though the flow rate of the stream 220 may be substantially constant and the time offsets dt1, dt2, dt3, dt4 determined carefully through calibration, there can still exist uncertainties in the arrival times of a micro-entity at a second interrogation point and each interrogation point or location along the stream 220 with respect to a trigger event initiated by the entity. The uncertainty in arrival times, or positions of the micro-entity, may be due to one or more types of motion-related errors.

Motion-related error of moving micro-entities may include any type and form of error that contributes to a deviation from an expected arrival time (or times) or expected location (or locations) of a micro-entity at a second location or second time (or additional locations or additional times) given the detection of the same micro-entity at a first location or first time. Motion-related errors of moving micro-entities may be due to real and/or apparent causes. Real motion-related error may comprise physical movement of a micro-entity within the stream from an expected location, e.g., energy coupled to the stream may perturb or dither the position of the micro-entity within the stream as it moves along the stream, even though the stream may flow without turbulence in some embodiments. Apparent motion-related error may comprise an observational effect that suggests movement of the micro-entity when there is no corresponding physical motion. Examples of apparent motion-related error may include, without being limited to, electronic detection effects (e.g., variable electronic delays, digitization errors) and optical effects (e.g., variable lensing effects due to an undulating fluidic stream).

In the field of flow cytometry, the motion-related errors associated with uncertainty in arrival times of micro-entities at interrogation points may be referred to as "pulse jitter." Pulse jitter provides one example of motion-related error for moving micro-entities in commercial systems, and can be visible when viewing signal pulses from the micro-entities on an oscilloscope. Pulse jitter can be due to real and/or apparent causes. An instance of pulse jitter is depicted by the late arrival of pulse 422, with respect to an expected peak arrival time $t_{21}$, as depicted in FIG. 4F. The inventors have found that pulse jitter can be observed without application of periodic energy to the stream 220 via transducer 212, and becomes markedly more pronounced with the application of periodic energy to the stream. Pulse jitter is observed to some degree on all multi-laser, SIA cell sorters currently in commercial use.

Figure 5:
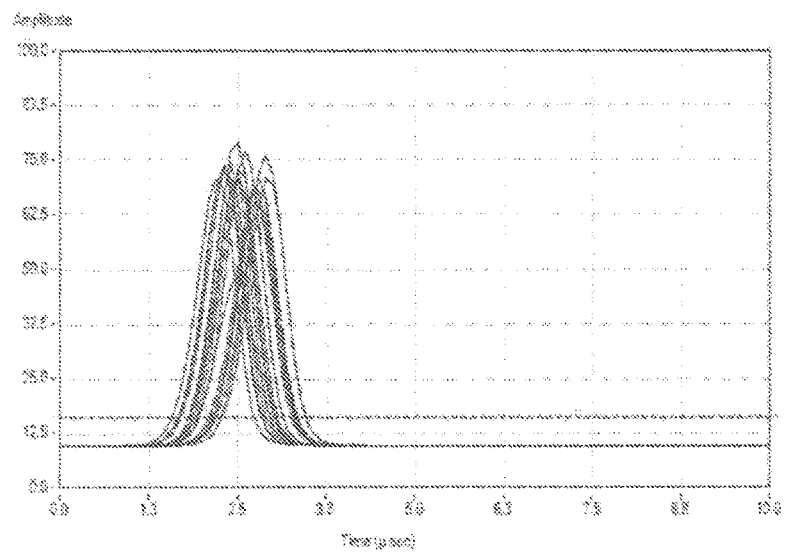
FIG. 5 is one example of pulse jitter observed in a flow cytometer.

An example of pulse jitter is depicted in FIG. 5. In FIG. 5, multiple pulses from multiple micro-entities observed at a same downstream location and triggered from nominally a same condition at an upstream location have been overlaid on the graph. The variations in pulse position on the plot reflects variations in arrival times at the downstream location and represents motion-related error in the system. The variations in arrival time can be greater than several pulse lengths in some systems. The variations in pulse position on the plot alternatively reflects an uncertainty in knowing the position of a micro-entity at a selected time.

In FIGS. 3C-3G, the observation windows 310, represented by vertical dashed lines, are sized to reflect the amount of pulse jitter at each interrogation beam location. As explained above, the observation windows are times at which data may be collected and ascribed to a same micro-entity that initiates a trigger pulse. The observation windows increase in size with distance from the nozzle, which reflects the observation that pulse jitter increases with distance from the nozzle. Greater amounts of pulse jitter require larger spans of time for the observation windows 310.

In various embodiments, the observation windows 310 are sized so that the majority of pulses generated by micro-entities at the corresponding interrogation point are captured within the observation window 310. In some embodiments, the observation windows 310 are sized so that a desired fraction of pulses generated by micro-entities at the corresponding interrogation point are captured within the observation window 310. A desired fraction may be between about 0.95 and about 1, between about 0.90 and about 0.95, between about 0.8 and about 0.9, between about 0.7 and about 0.8, or between about 0.6 and about 0.7 in various embodiments. In some implementations, if pulses arrive at a location with a distribution of times characterized by a standard deviation a, then the observation window 310 may be sized to be a first value that is proportional to an average width of the pulses, $w_{avg}$, plus a second value that is proportional to the standard deviation. For example, the width of the observation window, W, may be expressed by the following relation: $W = cw_{avg} + f\sigma$ where c is a real number greater than 0, and f is a real number greater than 0. If one of the terms is significantly greater than the other, an embodiment may have the window width determined by $cw_{avg}$ or $f\sigma$.

As may be appreciated, motion-related error (e.g., pulse jitter in a flow cytometer) can impose limits on system operation and throughput. For example, in order to correctly ascribe data from interrogation points to a correct micro-entity, each observation window would preferably not significantly overlap with a preceding window or a successive observation window in a data stream. In some instances, a small amount of overlap may be acceptable. In some implementations, there may be no overlap of observation windows, and there may be a buffer, or dead time, between each observation window. Maintaining a small overlap or preventing overlap of observation windows may place limits on the micro-entity throughput rate and/or the size of the interrogation region 222. For example, micro-entities in the stream 220 must be spaced far enough apart such that the observations may be correctly deconvolved and assigned to the micro-entity of interest at a desired probability or accuracy. In some implementations, the windows for successive micro-entities minimally overlap or do not overlap. Alternatively, or in addition, interrogation points must be constrained to a region near the nozzle orifice 208 where the amount of pulse jitter is within an acceptable limit.

Pulse jitter is found to be smallest when measuring pulses from interrogation points closest to the exit orifice 208, and corresponding data acquisition windows can have the shortest duration for interrogation points near the orifice while maintaining a desired level of measurement accuracy. The inventors have observed that the jitter increases appreciably with distance from the nozzle 202. This increase in jitter can impose limits on the size of the interrogation region 222. For example, the interrogation region may be restricted in size to where the jitter, for a given throughput, does not cause significant overlap of observation windows for a given throughput. In some systems, pulse jitter can restrict the total interrogation region to a small region of the stream (about 1 mm or less) close to the nozzle orifice 208. A limit on the size of the interrogation region can limit the number of interrogation beams that may be used in the system, and a limit on the number of interrogation beams constrains the analysis of the micro-entities.

Further, the inventors have found that jitter increases with the amplitude of the drive signal applied to the transducer 212. This increase in jitter may place a limit on how hard the transducer can be driven. Driving the transducer 212 with higher amplitudes may be desirable in some applications, since this generally leads to better uniformity and stability of droplet formation. However, an associated increase in pulse jitter may prevent driving the transducer with higher amplitudes at high throughput rates.

V. CHARACTERIZING MOTION-RELATED ERROR

A series of experiments were carried out to characterize motion-related error in a droplet cell-sorter flow cytometer, and to derive a model for the motion-related error. Since droplet generation was substantially periodic and sinusoidal (e.g., due to the form of the drive signal applied to the transducer 212), it was postulated that motion-related error for the flow cytometer may be correlated to the periodic perturbations applied to the stream 220, and that a model incorporating a periodic function may be representative of motion-related error in the system. Accordingly, it was postulated that pulse jitter J in the flow cytometer at any location along the stream 220 might exhibit an approximately sinusoidal correlation to a time offset $\Delta t_{dc}$ or phase $\varphi_{dc}$ measured from a reference or feature point in a drop clock cycle (e.g., a leading edge) to a reference point on a detected "trigger" pulse (e.g., a pulse peak or selected threshold value on a leading or trailing edge of the pulse).

For purposes of understanding and without being bound to any particular theory, this correlation may be expressed mathematically as follows:

$$J \sim A \sin(\Delta t_{dc} F + \theta) \tag{3}$$

where A is an amplitude that is to be determined, F represents the droplet generation frequency or frequency of the drop clock, and θ represents a phase that is to be determined. According to some embodiments, A and θ may be determined experimentally for a system in a calibration run. In other embodiments, A and θ may be determined on the fly as data is being accumulated by the system during the analysis and processing of useful samples. As will be apparent to those skilled in the art, other models (e.g., simple or higher-order Bessel functions, higher-order trigonometric functions, Gaussian functions, superposition of same or different functions) may be used to represent motion-related error in systems having moving micro-entities. It was also recognized that there could be additional components of motion-related error in the flow cytometer, such as errors introduced in the optical detection apparatus due to a moving and undulating stream and errors introduced in the electronics of the data acquisition system used to collect data from the interrogation points. Some of the additional components of error may or may not be represented by the same model. Some may require different models.

According to one embodiment, the jitter J for a flow cytometer can be measured on a system having a stream of moving micro-entities as a time offset from an expected arrival time in an observation window to an actual arrival time. The expected arrival time (e.g., times $t_1$, $t_2$, $t_3$, $t_4$ with reference to FIGS. 3C-3F) at any location in the stream 220 and observation window 310 may be established through a calibration procedure as described above. The observation window for the selected location may be set up to straddle the expected arrival time. The actual arrival time may be measured as a time at which a selected reference point on the pulse is detected. The choices of where an expected arrival time occurs within an observation window (e.g., beginning, middle, end) and what is used as a reference point on a pulse (e.g., leading edge threshold, peak, trailing edge threshold, integral threshold) may be dependent upon the particular implementation, and is less important for the development of a model for motion-related error, as long as the selected arrival time and reference point are used consistently.

Figure 6A:
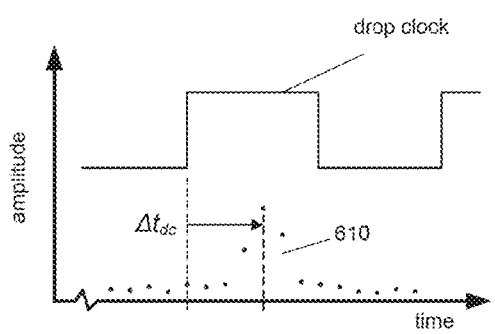
FIG. 6A depicts a delay of a trigger signal from a micro-entity detected at a first location as measured with respect to a reference signal in a flow cytometer, according to one embodiment.
Figure 6B:
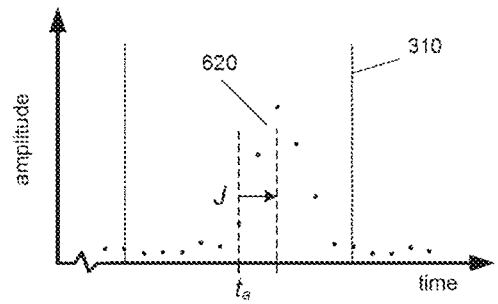
FIG. 6B depicts a corresponding variation in arrival time at a second location for the micro-entity observed in FIG. 6A.

For purposes of understanding aspects of the invention as applied to a flow cytometer, FIGS. 6A-6B graphically depict jitter J and the time offset $\Delta t_{dc}$ from the drop clock. FIG. 6A may represent a signal received from a trigger interrogation point, and FIG. 6B may represent a signal received from another interrogation point along the stream 220. Both values can be recorded in terms of clock cycles and converted to actual times by multiplying the clock cycles by the clock period, in some embodiments. For example, the time offset $\Delta t_{dc}$ and jitter J may be measured in terms of ADC clock cycles, drop clock cycles, or a combination thereof, as described above in connection with EQS. 1-2. In this example, the time offset $\Delta t_{dc}$ is measured from a rising edge of a drop clock to a peak of a detected trigger pulse 610. The jitter J is measured from an expected arrival time $t_a$ at the center of an observation window 310 to a peak of a second detected pulse 620. In some embodiments, the trigger pulse 610 may be generated by a micro-entity when it crosses a first beam B3 and the second detected pulse 620 may be a pulse detected from another interrogation point in the stream 220. In some embodiments, other reference points on the pulse, drop clock, and observation window may be used. If the postulated relation between pulse jitter and droplet generation were correct, then the observed jitter J for a plurality of micro-entities would be related to a measured time offset $\Delta t_{dc}$ according to the constructed error model, e.g. the model of EQ. 3.

Figure 7A:
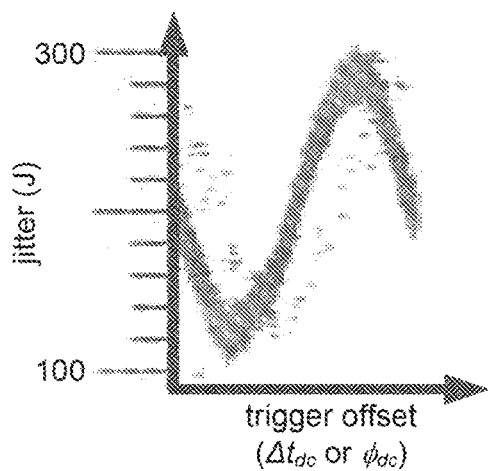
FIGS. 7A-7C are examples of jitter plots measured for a flow cytometer.

FIG. 7A shows a result of measurements of pulse jitter amplitude J as a function of time offset $\Delta t_{dc}$ or phase $\varphi_{dc}$ as recorded for a plurality of micro-entities in a flow cytometer. Plots of jitter data as depicted in FIG. 7A may be referred to as "jitter plots." The measurements were carried out on the sy3200™ system described above using calibration beads. The nozzle orifice was 70 microns in diameter and the pressure on the fluid was 50 psi. The droplet generation frequency was 84.9 kHz, and the jitter measurement was made using the interrogation beam farthest from the nozzle (about 2 mm from the nozzle). The resulting jitter plot clearly shows an approximately sinusoidal correlation between the jitter amplitude J and offset in trigger pulse timing $\Delta t_{dc}$.

Figure 7B:
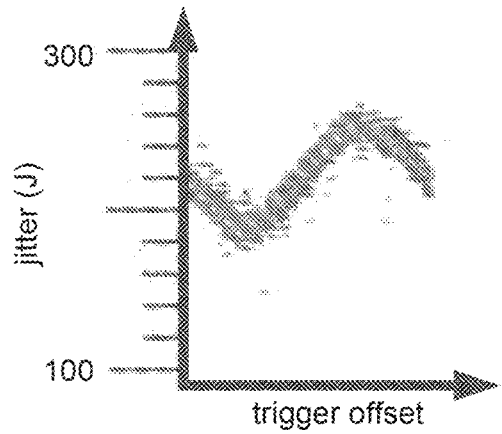

FIG. 7B shows results of jitter measurements under the same conditions as in FIG. 7A, but wherein the measurements were made using the interrogation beam second from farthest from the nozzle 212. The jitter plot shows a change in jitter amplitude (decreasing nearer the nozzle) but no change in phase θ of the jitter plot. For the plots in FIGS. 7A and 7B, a phase delay associated with the delay along the stream between the two interrogation points has been subtracted. The results indicate that the motion-related error, whether due to real or apparent causes, travels with the micro-entity along the stream at a same phase and increasing in amplitude.

Figure 7C:
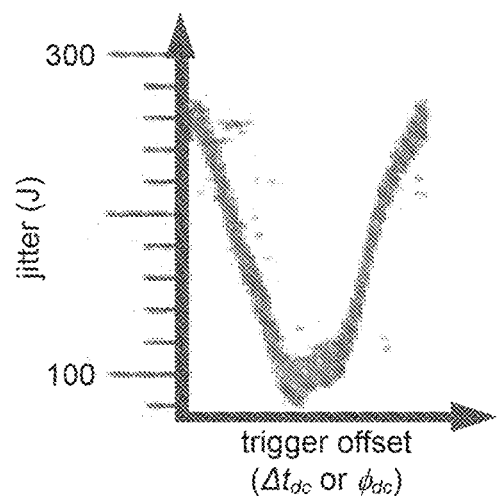

A change of phase θ of the jitter plot is observed in FIG. 7C. For this trial, the droplet frequency was changed to 77.9 kHz, and all other conditions were the same. The change in frequency resulted in a change of the jitter plot phase. A change in jitter plot phase is also observed when the position of the nozzle 212 is changed with respect to the location of the interrogation beam that is used as the trigger. No change in jitter plot phase, at any interrogation point, is observed when the amplitude of the transducer drive signal is altered.

A change in the amplitude of a jitter plot is observed when the amplitude of the transducer drive signal is altered. Also, as noted above, the amplitude of a jitter plot varies in relation to the distance of the interrogation beam from the nozzle. (Compare FIGS. 7A and 7B.) The amplitudes of jitter plots measured at beams farther from the nozzle are larger than amplitudes of jitter plots measured at beams closer to the nozzle.

The jitter plot results shown in FIGS. 7A-7C indicate that there is a predictive or deterministic component of motion-related error for micro-entities that may be corrected or compensated for in the flow cytometer system, or any system that is similarly configured. For example, if the time offset $\Delta t_{dc}$ from a feature point on the drop clock signal is measured for a trigger pulse, then a correction amount for adjusting the arrival time of a micro-entity at another location in the stream 220 can be computed from EQ. 3 and/or from the data of the jitter plots. The computed correction amount may be used, for example, to adjust the timing of observation windows 310 for each interrogation point for a micro-entity as it traverses the system. Such an adjustment may be used to re-center each observation timing window about an expected occurrence of each pulse. In terms of data streams emanating from the interrogation points, a computed correction amount may be used to adjust positions of the data segments within the data streams or memory addresses that store data that correspond to a signal for a same micro-entity. Because there is a predictive component of the pulse jitter, the predictive component may be compensated for in the system's data acquisition apparatus. The motion-related error itself may not be physically corrected. It will be appreciated that compensation for motion-related error may be carried out in other systems for which there is a predictable or deterministic component of motion-related error that can be modeled, e.g., represented by a mathematical model such as EQ. 3.

VI. JITTER COMPENSATION

Figure 8A:
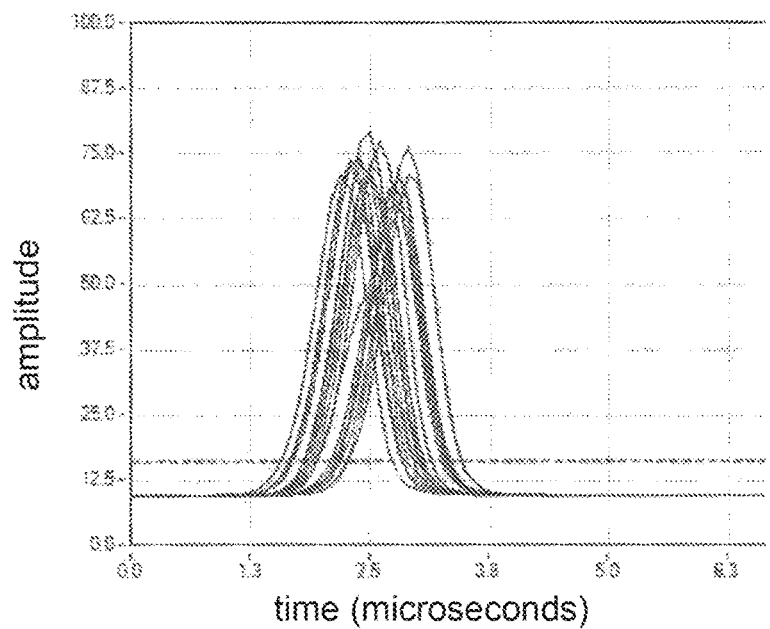
FIGS. 8A-8B show pulse jitter compensation, according to one embodiment.
Figure 8B:
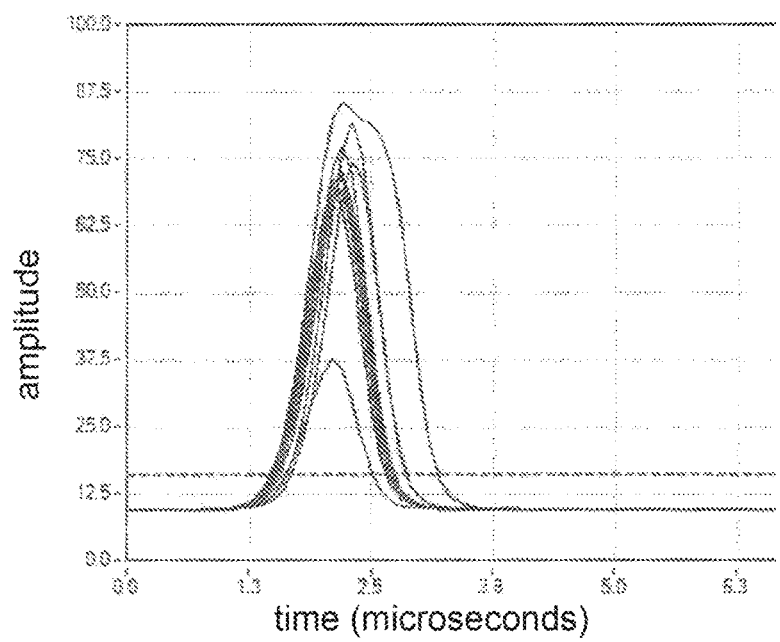

As described above for a flow cytometer, one component of motion-related error that is associated with the periodic coupling of energy to the stream 220 may be characterized and compensated for the system. Similar techniques may be applied to other systems, e.g., microfluidic systems. Results of jitter compensation, according to one embodiment in a flow cytometer, are shown in FIGS. 8A-8B. FIG. 8A shows pulse jitter as measured at one interrogation point in a flow cytometer system that operates in a conventional manner without jitter compensation. As can be seen in the overlay of pulses, the micro-entities arrive at the interrogation point with a distribution of times. For the non-compensated system, the pulse jitter of FIG. 8A is about 1 microsecond and more than a full-width-half-maximum value of the recorded pulses.

FIG. 8B shows similar data recorded for the same system in which jitter compensation is implemented. Compensation of jitter was achieved by using an error model (e.g., a model in accordance with EQ. 3, for example), and adjusting the timing of the data acquisition observation windows used to detect pulses at the interrogation point to minimize residual error. Further details of the implementation of motion-related error compensation in the flow cytometer system are described below. For the jitter-compensated data of FIG. 8B, the apparent jitter is reduced to a fraction of a pulse width. The results of FIG. 8B show that the component of pulse jitter that is primarily caused by the periodic perturbations introduced by the transducer 212 may be compensated in the data acquisition system. There may be residual components of pulse jitter that are not compensated by the above-described techniques (e.g., background jitter), which may be compensated for by alternative formulae to EQ. 3, or reduced by equivalent techniques.

It may be appreciated that compensation of motion-related error may be carried out in the data acquisition apparatus of a system. Variations in micro-entity arrival times may still occur in the physical system. In some embodiments, error compensation comprises changing the method by which pulses are observed, e.g., adjusting the timing of observation windows or the timing at which operations are performed on the micro-entities.

Further improvements may be made to the system. For example, as the dominant source of motion-related error is corrected for in a system, higher-order motion errors may become observable. The higher-order errors may in turn be characterized, modeled, and compensated for following processes described herein.

As may be appreciated from the foregoing discussions, measurement and characterization of motion-related errors for micro-entities in moving streams can be used to diagnose and improve system performance. Techniques for measuring and characterizing motion-related error are also described in a patent application filed concurrently by a common inventive entity and titled, "Characterization of Motion-Related Error in a Stream of Moving Micro-Entities," which is incorporated herein by reference in its entirety.

Figure 9:
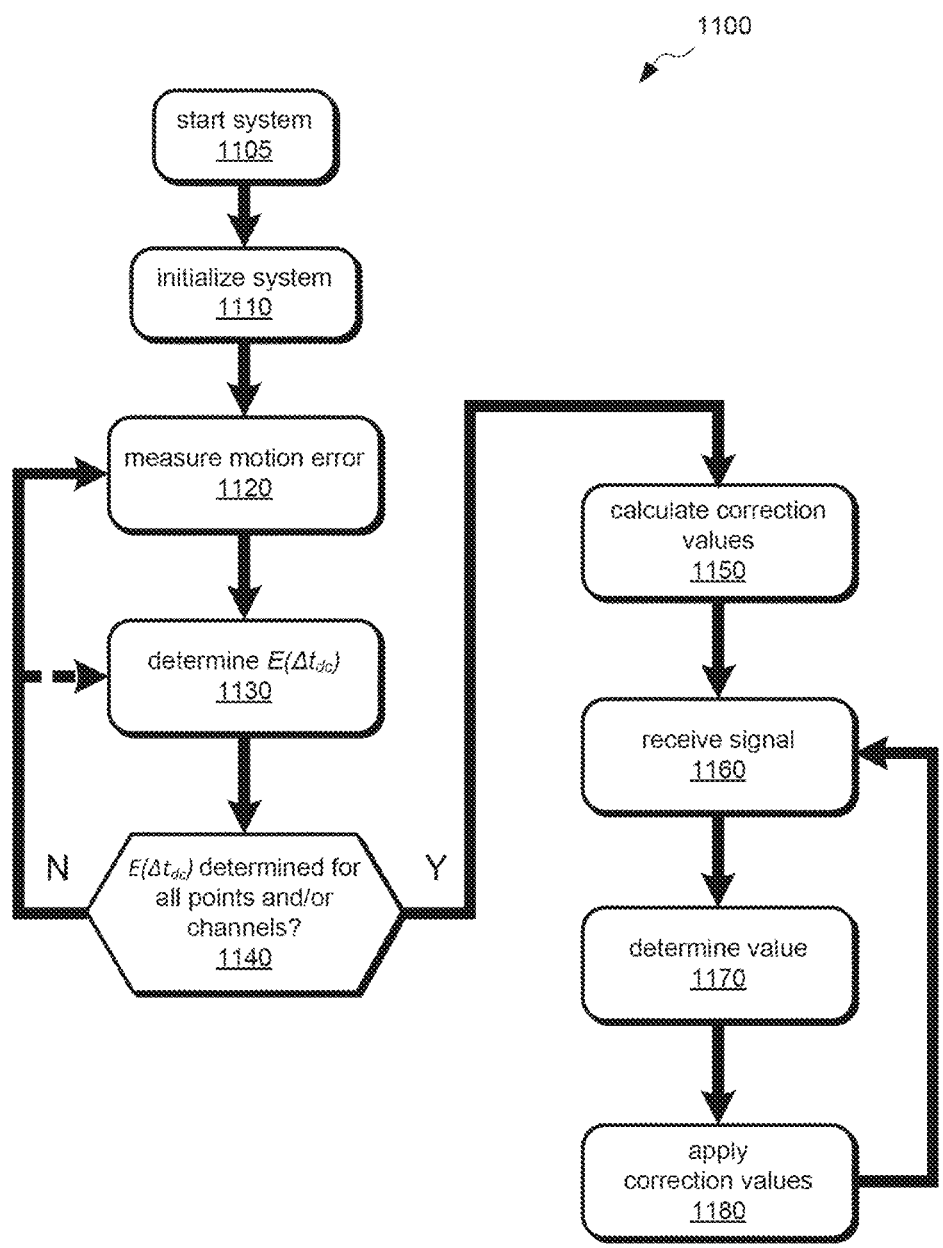
FIG. 9 depicts one embodiment of a method for characterizing and compensating motion-related error.

One embodiment of a method 1100 for characterizing and compensating motion-related error in a stream of moving micro-entities is depicted in the flow chart of FIG. 9. The steps shown in FIG. 9 may not all be included in various embodiments of methods for characterizing motion-related error. Some embodiments may only include a subset of the steps shown. Some embodiments may include additional steps not shown in the drawing, but described herein. Though the steps in FIG. 9 relate to characterizing and compensating pulse jitter in a flow cytometer, it will be appreciated that the method encompasses equivalent embodiments for characterizing motion-related error in other systems such as microfluidic and microfabrication systems.

According to one embodiment, a method 1100 for characterizing and compensating motion-related error may comprise starting 1105 a system in which micro-entities move from a first location to a second location or one or more additional locations. The system may be a flow cytometer, a microfluidic system, or any system configured to measure and/or operate on moving micro-entities. According to some embodiments, the system may be one in which microstructures are fabricated in fluidic streams, e.g., as in the systems described in U.S. patent application publication No. 2010/0172898 to Doyle et al. The method may include an act of initializing 1110 the system. The act of initializing may comprise verifying and/or setting operating parameters of the system, e.g., setting a velocity of the moving micro-entities. In a flow cytometer, the act of initializing 1110 may comprise performing calibrations for signal correlation and droplet membership as described above.

A method 1100 may further include measuring 1120 motion-related error, such as pulse jitter data. The measured motion-related error may be representative of deviations or variations in actual arrival times from expected arrival times. An expected arrival time of a micro-entity at a selected location may be based upon a separately detected event (e.g., a trigger event) that is caused by the micro-entity at a trigger location. The deviations in actual arrival times may be evaluated with respect to expected arrival times based on other considerations, e.g., average velocity of the micro-entities or average transit times between a "trigger" location and the measurement location. In addition to measuring the deviations of actual arrival times, the act of measuring 1120 motion-related error may include measuring an aspect of the trigger event (e.g., measuring an occurrence of a trigger event with respect to a system metric, such as a system reference signal or system clock, a pulse profile, a distance, or wavelength). In a droplet cell-sorting flow cytometer, an aspect of the trigger event may be its occurrence in time with respect to a reference point (e.g., rising edge) of a drop clock that is used to time the formation of droplets. In other embodiments, timing of a trigger event may be measured with respect to a timing of coupling energy into a stream in which the micro-entities are conveyed. In some embodiments, a system metric may include a sensed value, e.g., a temperature of the stream, a pressure of the fluid, an instantaneous velocity of the stream, an external acoustic level, an acceleration value measured for a system component.

Continuing with the example of the flow cytometer, measuring 1120 motion-related error may comprise measuring the following values for each pulse or micro-entity: drop clock phase (or time offset from a reference point on the drop clock) when the pulse arrives at a selected trigger channel, and time offset between the expected and actual pulse arrival times for a selected interrogation point or detection channel associated with the interrogation point. The collected data may be stored for processing by a next stage of method 1100.

In stating that measurements may be made for each of a plurality of micro-entities, it will be appreciated that the measurements may not be made for each and every micro-entity in the stream. The plurality of micro-entities may be a subset of the total number of micro-entities, and may refer to a portion of the micro-entities for which valid measurements are obtained for purposes of characterizing the motion-related error.

There may be several possible embodiments by which the pulse arrival time is measured at a selected trigger channel. One method is to measure the peak location of each pulse. Another embodiment is to measure the point at which the rising edge of a pulse crosses a selected threshold value. Yet another embodiment comprises measuring the point at which an integral of the pulse, i.e. the area under the pulse, crosses a selected threshold value.

In some embodiments, motion-related error data (such as jitter-plot data) may be acquired in error calibration and characterization runs. The error calibration and characterization runs may be executed after drop-delay calibration runs in some implementations. In other embodiments, motion-related error data may be acquired on the fly during an experiment in which micro-entities are being analyzed. When motion-related error data is collected on the fly, error characterization and compensation may be a dynamic process in which an error model is updated periodically based on observational data. Accordingly, error characterization and compensation may change over time to reflect any changes in collected error data. In some embodiments, the use of Bayesian priors may be useful to construct an initial error model and to support the updating of the error model given further observations of motion-related error in the system.

In some embodiments, characterization of motion-related error for any interrogation point in the stream 220 involves determining 1130 a relation between motion-related error E at a selected interrogation point and a measurable system quantity upon which the error may depend. Once the error data has been measured, the data may be processed to determine 1130 a relation between motion-related error E and a measurable system variable, e.g., an offset ($\Delta t_{dc}$ or $\varphi_{dc}$) of a trigger event with respect to a system reference signal, as described above for a flow cytometer. In some embodiments, the relation between E and $\Delta t_{dc}$ or $\varphi_{dc}$ may be determined empirically through error calibration and characterization measurements, e.g., measurements like those described above in connection with FIGS. 7A-7C. Calibration beads or fluorescent cells may be run through the system to obtain jitter plots, like those of FIGS. 7A-7C, for each interrogation point. In some implementations, the relation may be modeled by a function, e.g., identifying a function to fit the measured data.

A relation between motion-related error E and a measurable system variable may be determined 1130 for each point of interest in the stream of moving micro-entities. A point of interest may be a location in the stream at which a measurement is made of the micro-entity or an operation is performed on the micro-entity. In some embodiments, more than one measurement may be made at a point or location of interest. For example, in a flow cytometer there may be several detection channels for a single interrogation point. Because each detection channel in a system may exhibit different errors (e.g., different amounts of pulse jitter) in some cases, a relation between motion-related error E and a measurable system variable may be determined for each channel.

A method 1100 for characterizing and compensating motion-related error may include an act of determining 1140 whether a relation between motion-related error E and a measurable system variable (e.g., $\Delta t_{dc}$) has been evaluated for each point of interest, e.g., each interrogation point in the stream and each detection channel associated with each interrogation point. In some cases, there may be more than one detection channel per interrogation point, and method 1100 may include an act of determining 1140 whether a relation between motion-related error E and a measurable system variable has been evaluated for each detection channel. If a relation between motion-related error E and a measurable system variable has not been evaluated for each point of interest in the stream and/or detection channel, the method flow may return to a step of measuring 1120 motion-related error data for a next point of interest in the stream and/or detection channel. For an embodiment in which data for one or more points of interest are interpolated, the method flow may return to a step of determining 1130 a relation between motion-related error E and a measurable system variable, as indicated by the dashed arrow in FIG. 9. The error compensation values may be determined by interpolation techniques between measured end points. If a relation between motion-related error E and a measurable system variable has been evaluated for each point of interest in the stream and/or detection channel, the method flow may proceed to an act of calculating 1150 correction values that may be used to characterize and compensate the motion-related error.

According to some embodiments, calculating 1150 correction values comprises performing a curve fit to the measured error data. The measured error data may or may not be plotted on one or more graphs. One or more functions, e.g., a periodic function as in EQ. 3, may be fit to each plot or its corresponding data, and the resulting fitted functions may be used at each interrogation point to compensate for motion-related error in subsequent experimental runs. By determining parameters of the fitted function (e.g., amplitude, phase, delay, coefficients) characterization and compensation values can be computed from an analytical function for every pulse received.

Alternatively, motion-related error data for each interrogation point may be compiled and stored into look-up tables (LUTs), which may be used for each interrogation point to compensate for pulse jitter in subsequent experimental runs. In some embodiments, calculating 1150 correction values may comprise generating a look-up table of values, where each element of the LUT corresponds to a trigger phase or delay bin, and the value of each element is determined from the motion-related error data for the phase or delay bin. Possible methods for determining the value of each element in the LUT include, but are not limited to, computing the mean, median, and mode of the motion-related error data for that bin. An optional addition to this stage is to track the residual error and drive it to zero-mean. In some embodiments, this can be accomplished by recalculating the nominal offset so that the values in the LUT are zero-mean. This is accomplished by computing the mean of the measurement data, subtracting it from the data, and adding it to the nominal offset. In still other embodiments, a fraction of the nominal offset, e.g. ½ of said offset, is added to achieve a convergence to zero mean.

Figure 10A:
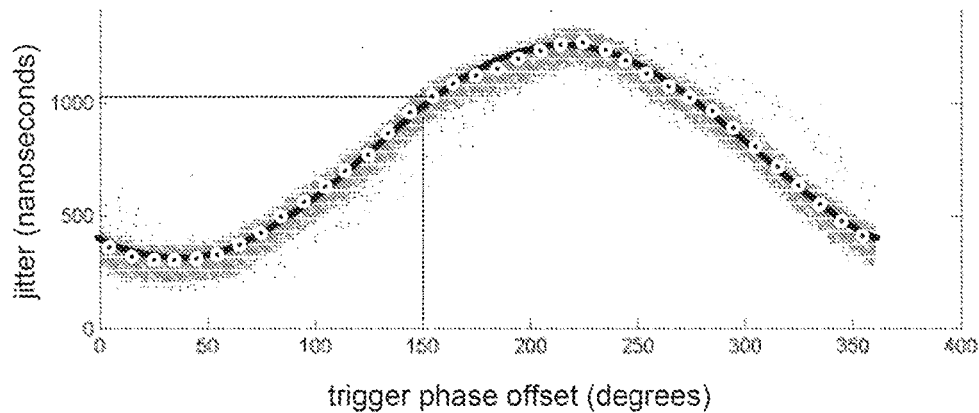
FIG. 10A shows a sinusoidal fit (black line) to a recorded jitter plot, according to one embodiment.

In some embodiments, the calculated LUT values may be limited in number where each LUT value may span a range of motion-related error conditions. Continuing with the above example of the flow cytometer, calculated LUT values may be limited to discrete trigger time or phase offset bins, e.g., 36 bins each spanning about 10 degrees of trigger phase offset values as depicted in FIG. 10A. Therefore, any measured trigger offset phase falling within a 10-degree bin would receive a same averaged value. As may be appreciated, trigger offset may be expressed in terms of time in some embodiments, e.g., time delay with respect to a reference point on the drop clock signal ($\Delta t_{dc}$), or may be expressed in terms of phase $\varphi_{dc}$, e.g., phase of the drop clock cycle.

In some embodiments, the act of calculating 1150 correction values may be executed on the fly during normal system operation, e.g., during a cell-sorting run, or in other embodiments it may be executed prior to normal operation, e.g., during a calibration run. As one example, a measured trigger offset may be used to compute a correction value from a functional fit on the fly. In the case of the flow cytometer described above, the act of calculating 1150 correction values may comprise calculating offset times that may be used to shift the time observation windows 310 for acquiring pulse data from each interrogation point. The calculated time offsets may be based on the motion-related error measurement data and may be such that the calculated offset time compensates for an average amount of motion-related error measured at a selected location. Calculated correction values may be used to compensate for a measured error and then discarded, or may be stored in a look-up table and accessed subsequently according to a measured trigger offset to compensate for motion-related error.

In some embodiments, a method 1100 for compensating motion-related error comprises receiving 1160 a signal from each micro-entity as each micro-entity crosses a first location, e.g., a trigger interrogation point. Each received signal may indicate a presence of each micro-entity at the first location, e.g., an arrival time. The signal may be a digital or analog signal received by at least one processor of the system.

A method for compensating motion-related error may further comprise determining 1170 for each first signal a value for each micro-entity with respect to a parameter of the system. According to one embodiment, the value may be a time or phase offset of an arrival time, as determined from the signal, of each micro-entity at the first location, wherein the time or phase offset is measured with respect to a metric of the system, e.g., a system clock, a reference signal provided by the system, a periodic signal provided by the system. In some embodiments, the metric of the system may be a sensed value, e.g., a temperature of the stream, a pressure of the fluid, an instantaneous velocity of the stream, an external acoustic level, an acceleration value measured for a system component. In some embodiments, the value may be associated with a component of an error model, developed from motion-related characterization measurements, that predicts the motion-related error associated with each micro-entity at one or more additional locations along a stream in the system.

The method 1100 for compensating motion-related error may further comprise applying 1180 the calculated correction values to compensate for motion-related error based upon the determined value. Correction values may be either calculated on the fly based on an error model, e.g., calculated in accordance with a functional fit to characterization data of the motion-related error, or may be selected from a LUT, e.g., using the determined value and/or an additional location of the stream as indices into the LUT. In some embodiments, a correction value may be applied to shift a data acquisition observation window 310, as described above. For example, a correction value may be used by a system processor to identify a segment of data within a data stream from an interrogation point that includes a signal for a micro-entity crossing that interrogation point. In some implementations, a correction value may be applied to determine more accurately a location of a micro-entity within a stream 220. In some embodiments, a correction value may be applied to adjust a time at which an operation is performed on a micro-entity, e.g., a sorting operation, an imaging operation, a probing operation, a transforming operation, etc.

In some embodiments, applying 1180 the calculated correction values may comprise employing interpolation techniques in conjunction with LUTs to compensate for motion-related error. For example, measurements may be made to determine LUT values for 10-degree bin increments as described above. The determined LUT values may then be stored in a LUT data store for subsequent use. After receiving 1160 a signal and determining 1170 a value for a micro-entity, the LUT may be accessed using the determined value as an index into the table. If the value corresponds to an existing time or phase offset index for the LUT, then a corresponding correction amount may be returned. If the determined value does not correspond to an existing time or phase offset, then an interpolation process may be used to compute a correction amount. The interpolation process may use two correction amounts from the LUT that correspond to indices nearest the determined value from the received signal. Interpolated values may be computed by processor 250 based upon linear or higher-order interpolation. The interpolation may be executed in a field-programmable gate array in some embodiments. An interpolated value, rather than a specific LUT value, may then be used to compensate for motion-related error for the micro-entity.

According to some embodiments, the acts of receiving 1160, determining 1170, and applying 1180 may be executed for each micro-entity traversing the system at high repetition rates. In some systems, the repetition rates may be as high as 50,000 executions per second, greater than approximately 50,000 executions per second in some embodiments, greater than approximately 100,000 executions per second in some embodiments, and yet greater than approximately 150,000 executions per second in some embodiments. In some implementations, the act of applying may be repeated for a single micro-entity at one or more additional locations along the stream. For example, the value that is determined in the act of determining 1170 may be used to determine one or more correction values for each of the one or more additional locations.

In some embodiments, the acts of measuring 1120 motion-related error, determining 1130 a relation between error E and a measurable system variable, and calculating 1150 correction values may be done in parallel for each interrogation point and data acquisition channel in the system. In such embodiments, the act of determining 1140 whether a relation between error E and a measurable system variable has been evaluated for each point of interest may not be needed.

In some implementations, the acts of measuring 1120 motion-related error data and determining 1130 a relation between motion-related error E and a measurable system variable may be done in real time, e.g., during a normal sorting run in which micro-entities are analyzed. Motion-related error data acquired in real time may be processed and used to calculate error compensation values as the system is running. In some embodiments, the calculated values may be used subsequently to compensate motion-related error. In such implementations, separate calibrations runs for measuring and characterizing motion-related error may not be necessary, or any motion-related error compensation data previously calculated may be updated in real time during a normal run. In some embodiments, the use of Bayesian statistics can provide a useful framework for real-time updating of an error model for the system.

In some embodiments, the acts of measuring 1120 motion-related error data, determining 1130 a relation between error E and a measurable system variable, and calculating 1150 correction values may be executed for each point or location of interest and/or each detection channel. The measured data may be processed separately. For example, data from each measurement may be fit to a functional form, or may be compiled into a look-up table specific to the location and/or channel corresponding to the measured data.

As noted above, any one of the interrogation points in a stream may be used as a trigger interrogation point when data from the interrogation points are buffered. Accordingly, a system may be configured to determine correction values based upon one trigger interrogation point (e.g., the first interrogation point encountered along the stream from the flow cytometer nozzle), and subsequently change operation to use another interrogation point (e.g., the second interrogation point) as the trigger interrogation point. In some embodiments, it may not be necessary to execute a re-calibration procedure on the system to determine correction values for the new trigger interrogation point. Instead, the stored correction values, functional fit, or LUT may be transformed mathematically to reflect the change in trigger interrogation point. According to one embodiment for a flow cytometer, if the correction values are implemented as LUTs indexed by a phase or time offset that is determined when a particle crosses the trigger point, and the trigger interrogation point is changed from the first interrogation point along the stream to the second point along the stream, then the following mathematical transformation may be applied: first, the original LUT values for the second interrogation point are subtracted from each of the interrogation point LUTs on a per-bin basis. For the second interrogation point, this subtracts the original LUT values from themselves, which correctly leaves zero values in the LUT for the new interrogation point. Second, each of the new LUTs for other interrogation points must be circularly shifted by a number of bins equivalent to a phase difference between the first and second interrogation points that has been determined for the current drop clock frequency and stream velocity.

Since it is possible for multiple data acquisition channels to be used for a selected interrogation point and for all of these channels to have substantially equivalent motion-related error characteristics, it may be beneficial to reconcile the pulse jitter measurement data across these common channels. One embodiment comprises selecting one of the common channels at an interrogation point (e.g., a channel with a best signal-to-noise ratio for the detected micro-entities) to use for determining motion-related error values. According to another embodiment, all motion-related error data measured for all channels at an interrogation point may be combined before calculating the correction values. Yet another method comprises computing a metric for each channel that indicates how well the correction values fit the measurement data, and select the correction values from the channel with the best metric. By way of example, the metric may use a mean-squared error (MSE) or root-mean-squared error (RMSE) algorithm, or may compute a total residual error.

In some implementations, determining 1130 a relation between motion-related error E and a measurable system variable and/or calculating 1150 correction values may comprise measuring motion-related error data at a first interrogation point and at a second interrogation point. There may be one or more interrogation points between the first and second interrogation points. According to some embodiments, data for the one or more points between the first and second points may be interpolated from the data measured for the first and second interrogation points. The interpolation may follow a linear model, non-linear model, or a selected functional form. The data for each point, whether measured of interpolated, may be fit to a functional form, or may be compiled into a look-up table specific to each interrogation point.

In terms of system hardware and/or software and referring to FIG. 2, motion-related error characterization and compensation may be implemented with a combination of one or more processors 250, data acquisition device 230 and memory 240. According to one embodiment, motion-related error characterization and compensation may be implemented by adjusting the timing of data acquisition windows opened for the detection of pulses by data acquisition device 230 after detection and processing of a trigger event. Processor 250 may identify a trigger event, e.g., a pulse from detector D1, and compare a reference point (e.g., a leading edge threshold value) on the trigger pulse with a reference point (e.g., a rising edge) on the drop clock. Based on a time difference between these two events, processor 250 may adjust the timings of observation windows opened by the data acquisition device 230 to receive pulse data from other interrogation point detectors D2, D3, D4, D5. The observation windows may be advanced in time or delayed.

According to another embodiment, all data received from the interrogation point detectors may be temporarily stored to a memory 240, e.g., a FIFO or ring buffer memory. Processor 250 may be configured to select data segments from each detector data stream based upon the timing of a trigger event with respect to the drop clock, e.g., based upon a measured value for time offset $\Delta t_{dc}$ or drop clock phase $\varphi_{dc}$.

As noted above for a flow cytometer, there are aspects of the jitter plots that depend upon certain system conditions. The amplitude of a jitter plot may depend upon an amplitude or amount of energy coupled from the droplet transducer 212 into the stream 220 and upon the distance of the interrogation point from the nozzle or transducer. The phase of a jitter plot may depend upon a frequency of the drop drive signal and also upon a distance of the trigger interrogation point from the nozzle. Therefore, if the amplitude of the drop-drive signal, frequency of the drop-drive signal, and/or distance of the interrogation point from the nozzle change, then the system may need to be recalibrated to obtain an updated model for the motion-related error. In a system configured for on-the-fly error data collection, characterization, and compensation, characterization and compensation values may be continuously updated so that the system tracks changes in amplitude of the drop-drive signal, frequency of the drop-drive signal, and/or distance of the interrogation point from the nozzle so that separate error re-calibration runs may not be needed.

Characterization and compensation of motion-related error has several beneficial aspects for a system having a stream of moving micro-entities. Characterization of motion-related error can permit the error to be modeled and reduced by employing compensation techniques. Compensation of motion-related error in data analysis can reduce the width of the observation windows 310 at any interrogation point. Reduction of observation windows can permit detection, measurement, and sorting of micro-entities with closer spacing in the stream and thus allow higher throughput for the system.

One benefit associated with characterizing and compensating motion-related error (e.g., pulse jitter) in a flow cytometer relates to the detection apparatus for detecting the micro-entities. Because pulse jitter can be compensated in a flow cytometer, larger amounts of pulse jitter can be tolerated in the system. Accordingly, the interrogation points can be spaced farther apart in the stream. In some embodiments, the interrogation region can extend over 2 millimeters. The increased spacing of interrogation points reduces the cross-talk of signals from each interrogation point, thereby improving the signal-to-noise ratio for each interrogation point.

Characterization and compensation of motion-related error can also improve the accuracy in determination of drop membership for each micro-entity, since deviations of the position of a micro-entity from a central location within a segment of the stream 220 that will form a droplet are better determined. Narrow observation windows can allow finer resolution for determining the position of a micro-entity within a segment of the stream that will form into a droplet. Knowing the position of a micro-entity within a segment with finer resolution improves determination of drop membership. A more accurate determination of drop membership can improve sort quality, e.g., sort purity.

Sort purity may also be improved by better resolution of doublets or muliplets. Some stream segments that will form droplets may carry more than one micro-entity. Narrower observation windows may allow doublets or multiplet to be more clearly resolved, e.g., indicating the presence of more than one micro-entity within a droplet whereas a previous system may have only indicated one entity. Narrower observation windows may also allow better determination of which drop a micro-entity will end up in if the micro-entity is near a stream-segment boundary between two droplets to be formed.

As noted above, motion-related error characterization and compensation may allow larger interrogation regions 222. For example, flow cytometers which could not tolerate large amounts of pulse jitter that occur at greater distances from the nozzle (e.g., greater than about 1 mm, greater than about 1.5 mm) may use jitter characterization and compensation techniques to mitigate undesirable effects of pulse jitter. Larger observation regions can permit additional interrogation beams to be used for more complex analysis of the micro-entities.

VII. MODULATION OF STREAMS OF MOVING MICRO-ENTITIES

In the flow cytometer embodiments described above, acoustic energy is coupled to a stream that conveys micro-entities for purposes of forming droplets so that the micro-entities may be contained within droplets that may be sorted according to an applied charge. The acoustic energy is coupled to the stream 220 according to a regular periodic cycle, but the micro-entities arrive in the stream 220 at random times. The application of periodic acoustic energy to the stream assists in the control of the individual micro-entities that arrive randomly in the stream, e.g., assists in identifying and sorting each micro-entity. Although the coupling of acoustic energy introduces an amount of motion-related error to the system, in the form of pulse jitter for the flow cytometer, the error has a deterministic nature, as shown in FIGS. 7A-7C, for example, which allows for compensation of the error to enable more accurate analyses of the micro-entities and higher system throughput.

There may exist other areas of technology in which application of acoustic energy to a stream of moving micro-entities may be beneficial for micro-entity analysis and control. For example, in microfluidic systems that may be used for analyses or manufacture of micro-entities, periodic acoustic energy may be coupled to channels through which the micro-entities move. Although micro-entities may arrive randomly in a channel, the periodic acoustic energy and error compensation techniques described above may be used to better determine the location of individual micro-entities within the channel, or a time at a selected location at which to perform an operation on a micro-entity. Knowing a location of a micro-entity within a channel or an arrival time of the micro-entity at a selected location more accurately may improve analysis and or sorting operations of the microfluidic system. Acoustic energy may be coupled into a channel through integrated acoustic transducers located on a microfluidic chip, in some embodiments.

In some embodiments, acoustic energy coupled to a stream of moving micro-entities may improve imaging of the micro-entities. For example, a system may be configured to image micro-entities flowing in a stream using a time delay integration (TDI) multi-pixel imaging device. One example of TDI imaging is described in U.S. Pat. No. 6,608,680 to D. Basiji et al, which is incorporated herein by reference. Knowing more accurately successive locations of a micro-entity moving in a stream allows better alignment of successive images formed of the moving micro-entity. Better alignment of successive images can be used to reduce image noise and improve image resolution.

VIII. EXAMPLES

By way of instruction, and without being bound to any particular implementation, examples of detecting an compensating pulse jitter in a flow cytometer are described in the following example.

Example 1

In this example, a droplet cell sorter was configured with a light collection optic referred to as Reflection Collection Optic-5 (RCO-5) that enables probing of and light collection from five interrogation points along the stream 220. (RCO-5 is available from iCyt Mission Technology, 2100 South Oak Street, Champaign, Ill. 61820, USA). The RCO-5 permits various separation distances among the interrogation points. In this example, the vertical distance (the length of the path a cell would travel from a top interrogation point (#1) to the bottom interrogation point (#5) is 2 mm. The RCO-5 was tested with droplet cell sorter nozzles having orifice diameters of 70, 100, and 126 microns and various stream velocities from 10 m/s to 40 m/s. Pulse jitter was measured by utilizing a data acquisition system (product BW-5) from an iCyt Reflection System (available from iCyt Mission Technology, 2100 South Oak Street, Champaign, Ill. 61820, USA). This data acquisition system digitally samples the analog signal produced by the cell sorter's detectors (Hamamatsu photomultiplier tubes (PMTs) with 45 MHz bandwidth) at 105 MHZ. Pulse jitter was assessed by measuring the Δt between the crossing of the leading edge of the pulse at 10% peak height for a signal produced at interrogation point #2 and a signal from the same micro-entity at interrogation point #5. All five interrogation points were within about 2 mm of the nozzle orifice 208. Droplets did not separate from the stream until about 6 mm from the nozzle orifice.

When the droplet generator was not active (i.e., the stream passed into a waste vessel without separating into droplets), the jitter was observed to be less than 100 ns. When the droplet generator was engaged, various amounts of jitter were recorded for each operating point (combination of sheath pressure, droplet frequency, droplet transducer drive intensity). The highest value of pulse jitter observed was a total variation of 3 microseconds (or approximately three times the average width of the pulses).

The following observations were also made: (1) without droplet generation (i.e., just a flowing stream) the Δt for any two spots is almost constant; (2) when droplet generation is turned on significant variations in Δt are observed between the first and last (farthest separated) interrogation points, and may in some cases be as much as 4 pulse lengths; (3) the amount or severity of pulse jitter increases with increase in droplet transducer drive amplitude; and (4) the amount or severity of pulse jitter increases as the droplet break-off point moves closer to the exit of the nozzle.

Data that was collected in the laboratory experiments were subjected to analyses to determine: (a) how well a sine function could be fit to the data, and (b) whether a fitted sine function could be used to adequately correct the observed jitter. Results of these analyses appear in FIGS. 10A-10B. In FIG. 10A, a jitter plot is shown for measurements obtained from an interrogation point farthest from the nozzle (interrogation point #5). The recorded data represent measured jitter (in nanoseconds) as a function of trigger pulse offset from a reference point on the drop clock signal, expressed as phase. Shown in the plot are both a least-squares sinusoidal curve fit to the data (black line) and bin averages from a look-up table computation (white circles). In this example, the LUT values were calculated by taking an average value of the jitter data within discrete phase-angle bins. The phase-angle bins each spanned about 10 degrees. Though both the fitted function and LUT values represent the measured data well, the LUT values may more accurately characterize the jitter. For example, the LUT values reflect higher-order effects in the jitter data that is more clearly visible near the maximum and minimum values of the jitter plot.

Figure 10B:
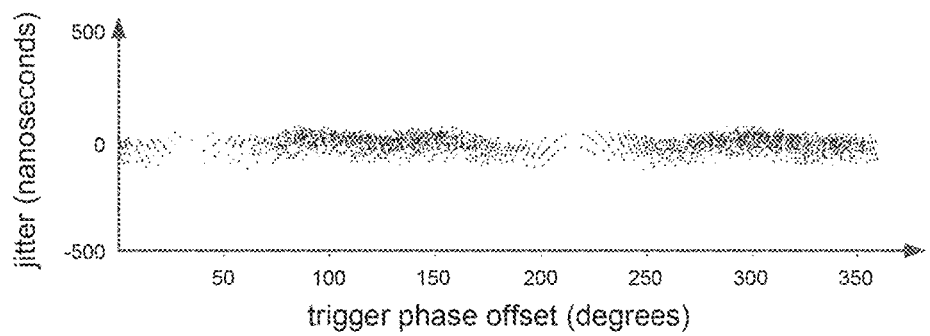
FIG. 10B represents the jitter data of FIG. 10A compensated according to the sinusoidal fit.

In FIG. 10B, the measured jitter data of FIG. 10A has been corrected using the sinusoidal fit to the data. The result is an effective reduction or compensation of pulse jitter from about 1000 nanoseconds to about 200 ns. The histograms plotted in FIGS. 11A and 11B correspond to the respective data of FIGS. 10A and 10B.

Figure 11A:
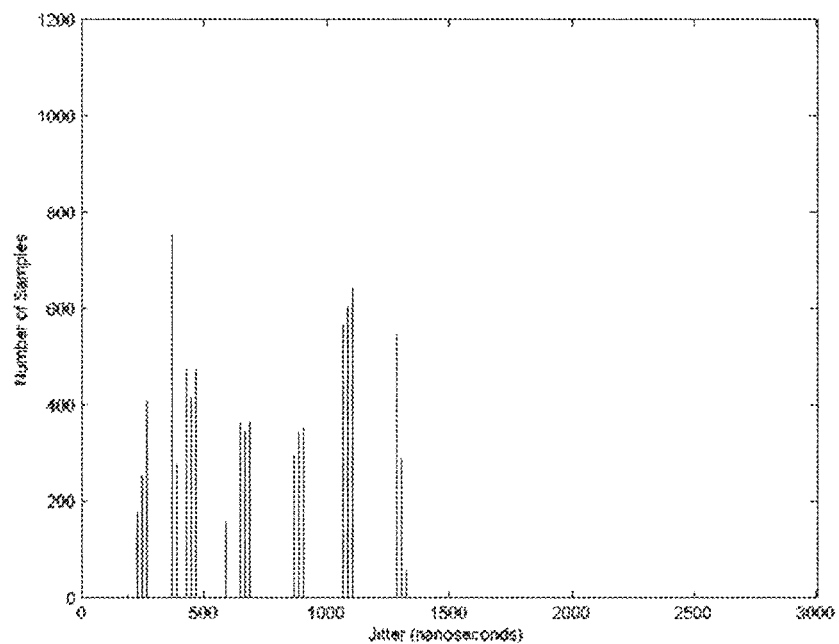
FIG. 11A is a histogram of the jitter data of FIG. 10A.
Figure 11B:
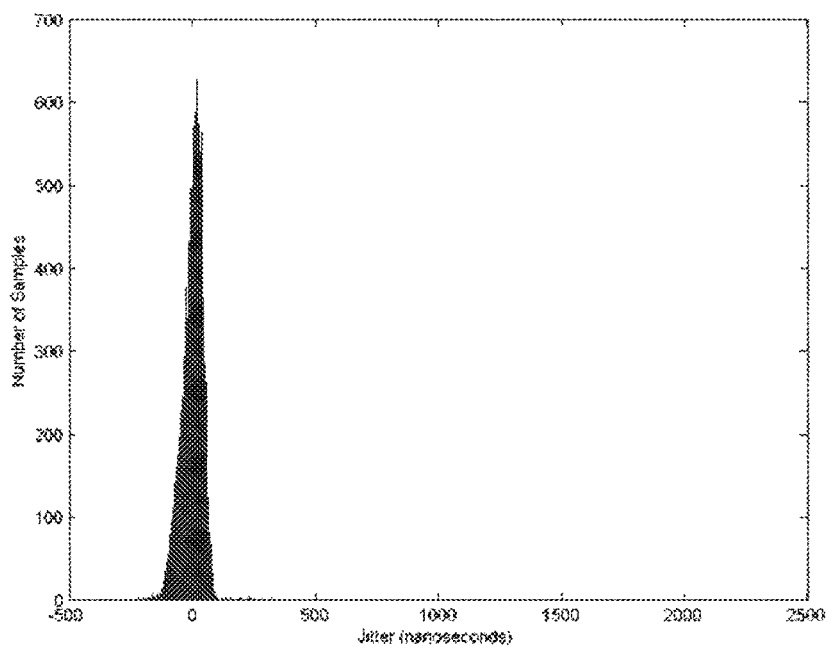
FIG. 11B is a histogram of the compensated jitter data of FIG. 10B.

The histogram of FIG. 11A indicates that pulses in a system that has no jitter compensation are distributed over a window greater than about 1000 nanoseconds in width. When jitter compensation is applied to the system, the FWHM distribution of pulses is less than about 100 ns, as shown in FIG. 11B.

In view of these results, a data acquisition window would need to be at least 1.5 microseconds wider (in duration) than the pulse width to capture pulses with the amount of jitter shown in FIGS. 10A and 11A. However, by compensating or correcting the jitter as shown in FIGS. 10B and 11B (e.g., by adjusting the timing of the data acquisition window), the window need only be as little as 100 ns wider than the pulse width.

IX. CONCLUSION

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, system upgrade, and/or method described herein. In addition, any combination of two or more such features, systems, articles, materials, kits, and/or methods, if such features, systems, articles, materials, kits, system upgrade, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., analysis of detected pulses, calibration, and compensation of pulse jitter, may be embodied and/or implemented at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays (FPGAs) or other semiconductor devices, or other tangible computer storage medium or non-transitory medium) encoded with one or more programs that, when executed on one or more computers or other processor(s), perform methods that implement the various embodiments of the technology discussed above. The computer readable medium or media can be transportable, such that the program or programs stored thereon can be loaded onto one or more different computers or other processors to implement various aspects of the present technology as discussed above. As one example, in some embodiments processing of data and system operation may be implemented entirely, or at least in part, in FPGAs.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A system for compensating motion-related error associated with micro-entities that move inside a fluid stream crossing a first location and at least a second location, the system comprising:
   detection apparatus configured to generate a first signal when a micro-entity moving inside the fluid stream crosses the first location and generate at least a second signal when the micro-entity moving inside the fluid stream crosses at least the second location, wherein the first signal includes measurement data associated with the micro-entity during the crossing of the first location;
   one or more processors configured to:
   receive the first signal;
   determine from the first signal a value with respect to a parameter of the system as a function of the measurement data of the first signal; and
   adjust, by a correction amount that compensates for motion-related error associated with the micro-entity, an observation or operation time for observing or operating on the micro-entity at the second location, wherein the correction amount is determined from an error model that predicts the motion-related error associated with the micro-entity as a function of the determined value.

2. The system of claim 1, wherein the one or more processors is or are further configured to adjust, by at least one additional correction amount that compensates for motion-related error associated with the micro-entity, respective one or more observation or operation time or times for observing or operating on the micro-entity at respective one or more additional locations, wherein the at least one additional correction amount is determined from the error model using the determined value.

3. The system of claim 1, wherein the micro-entities move in a fluid stream of a flow cytometer or a microfluidic device.

4. The system of claim 1, wherein the value determined with respect to a parameter of the system is a time or phase offset measured between an arrival time of the micro-entity at the first location and a reference signal of the system.

5. The system of claim 4, wherein the time or phase offset is measured using a number of clock cycles of a clock signal provided by the system.

6. The system of claim 4, wherein the reference signal comprises a periodic signal produced by the system.

7. The system of claim 6, wherein the periodic signal is used to couple energy to a stream that conveys the micro-entities between the first location and the second location.

8. The system of claim 7, wherein the periodic signal is derived from a drop clock that is used to time the formation of droplets in a flow cytometer.

9. The system of claim 1, further comprising a transducer configured to couple energy periodically to a stream that conveys the micro-entities between the first and second locations, and wherein the value is determined with respect to a feature of a signal that drives the transducer.

10. The system of claim 1, wherein the first and at least second locations are spaced apart more than approximately 1 millimeter.

11. The system of claim 10, further comprising one or more sources of radiation configured to probe the micro-entities at the first and at least second locations.

12. A manufactured data-storage device embodying machine-readable instructions that, when executed by at least one processor, adapt the at least one processor to:
- receive a first signal indicating a presence of a micro-entity moving inside a fluid stream at a first location in a system in which micro-entities move inside the fluid stream when the micro-entity crosses the first location on its way to at least a second location, wherein the first signal includes measurement data associated with the micro-entity during the crossing of the first location;
- determine from the first signal a value with respect to a parameter of the system as a function of the measurement data of the first signal; and
- adjust, by a correction amount that compensates for motion-related error associated with the micro-entity with respect to the fluid stream, an observation or operation time for observing or operating on the micro-entity at the second location, wherein the correction amount is determined from an error model that predicts the motion-related error associated with the micro-entity as a function of the determined value.

* * * * *